(12) United States Patent
Greenberg et al.

(10) Patent No.: US 11,172,913 B2
(45) Date of Patent: Nov. 16, 2021

(54) SYSTEM AND METHOD FOR TISSUE RETRIEVAL

(71) Applicant: BRIGHAM AND WOMEN'S HOSPITAL, Boston, MA (US)

(72) Inventors: James Greenberg, Weston, MA (US); Jon Einarsson, Boston, MA (US); Ron Adams, Holliston, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 594 days.

(21) Appl. No.: 15/101,162

(22) PCT Filed: Dec. 2, 2014

(86) PCT No.: PCT/US2014/068019
§ 371 (c)(1),
(2) Date: Jun. 2, 2016

(87) PCT Pub. No.: WO2015/084769
PCT Pub. Date: Jun. 11, 2015

(65) Prior Publication Data
US 2016/0302783 A1    Oct. 20, 2016

Related U.S. Application Data

(60) Provisional application No. 61/910,878, filed on Dec. 2, 2013, provisional application No. 61/950,274, filed
(Continued)

(51) Int. Cl.
*A61B 17/00* (2006.01)
*A61B 90/40* (2016.01)

(52) U.S. Cl.
CPC ........ *A61B 17/00234* (2013.01); *A61B 90/40* (2016.02); *A61B 2017/00287* (2013.01)

(58) Field of Classification Search
CPC .............. A61B 17/00234; A61B 90/40; A61B 2017/00287
See application file for complete search history.

(56) References Cited

U.S. PATENT DOCUMENTS 4,694,827 A * 9/1987 Weiner ................. A61F 5/0036
604/909
5,037,379 A * 8/1991 Clayman .......... A61B 17/00234
128/849

(Continued)

OTHER PUBLICATIONS

International Search Report and Written Opinion dated Mar. 4, 2015 in connection with PCT/US2014/068019.

*Primary Examiner* — Phong Son H Dang
(74) *Attorney, Agent, or Firm* — Quarles & Brady LLP

(57) ABSTRACT

Embodiments of the invention provide a retrieval device and method for retrieving tissue from a body cavity. The retrieval device includes a pouch having an aperture and a pouch wall defining an interior space. An inflatable rim is coupled to the pouch and facilitates retrieval of the tissue into the interior space of the pouch. The retrieval device further includes a closure device coupled to the pouch wall for enclosing the tissue within the interior space of the pouch. A portion of the pouch wall includes a self-sealing characteristic that allows an instrument to pierce the pouch wall and the pouch wall is resealable after withdrawal of the instrument. The pouch can move from a retracted position to a expanded position upon inflation of the inflatable rim, which can then be separated by application of a separation force at an area of material weakness in the pouch wall.

22 Claims, 16 Drawing Sheets

Related U.S. Application Data on Mar. 10, 2014, provisional application No. 62/018,176, filed on Jun. 27, 2014.

(56) References Cited

U.S. PATENT DOCUMENTS

| | | | |
|---|---|---|---|
| 5,224,930 A | 7/1993 | Spaeth et al. | |
| 5,499,988 A | 3/1996 | Espiner | |
| 5,735,289 A * | 4/1998 | Pfeffer | A61B 17/00234 600/562 |
| 6,685,628 B2 * | 2/2004 | Vu | A61B 17/00234 600/37 |
| 8,409,217 B2 * | 4/2013 | Parihar | A61B 17/00234 606/127 |
| 9,370,341 B2 * | 6/2016 | Ceniccola | A61B 17/00234 |
| 2009/0192510 A1 * | 7/2009 | Bahney | A61B 17/32056 606/45 |
| 2010/0152746 A1 | 6/2010 | Ceniccola et al. | |
| 2010/0219091 A1 * | 9/2010 | Turner | A61B 17/00234 206/438 |
| 2011/0184311 A1 * | 7/2011 | Parihar | A61B 17/00234 600/562 |
| 2011/0184432 A1 | 7/2011 | Parihar et al. | |
| 2011/0184434 A1 * | 7/2011 | Parihar | A61B 17/00234 606/114 |
| 2011/0190780 A1 * | 8/2011 | O'Prey | A61B 17/26 606/114 |
| 2011/0190781 A1 * | 8/2011 | Collier | A61B 17/00234 606/114 |
| 2011/0196195 A1 * | 8/2011 | Raven | A61F 5/0056 600/37 |
| 2012/0109144 A1 | 5/2012 | Chin et al. | |
| 2012/0165611 A1 * | 6/2012 | Warren | A61B 17/3421 600/204 |
| 2012/0203241 A1 * | 8/2012 | Williamson, IV | A61B 10/06 606/114 |
| 2013/0131689 A1 * | 5/2013 | Farascioni | A61B 17/00234 606/114 |
| 2013/0184536 A1 * | 7/2013 | Shibley | A61B 17/00234 600/235 |
| 2014/0236110 A1 * | 8/2014 | Taylor | A61J 1/10 604/327 |
| 2014/0236168 A1 * | 8/2014 | Shibley | A61B 17/0218 606/114 |
| 2014/0330285 A1 * | 11/2014 | Rosenblatt | A61B 17/00234 606/114 |
| 2015/0216519 A1 * | 8/2015 | Tang | A61B 17/3423 600/204 |
| 2016/0008081 A1 * | 1/2016 | Forsell | A61B 17/3423 600/204 |

* cited by examiner

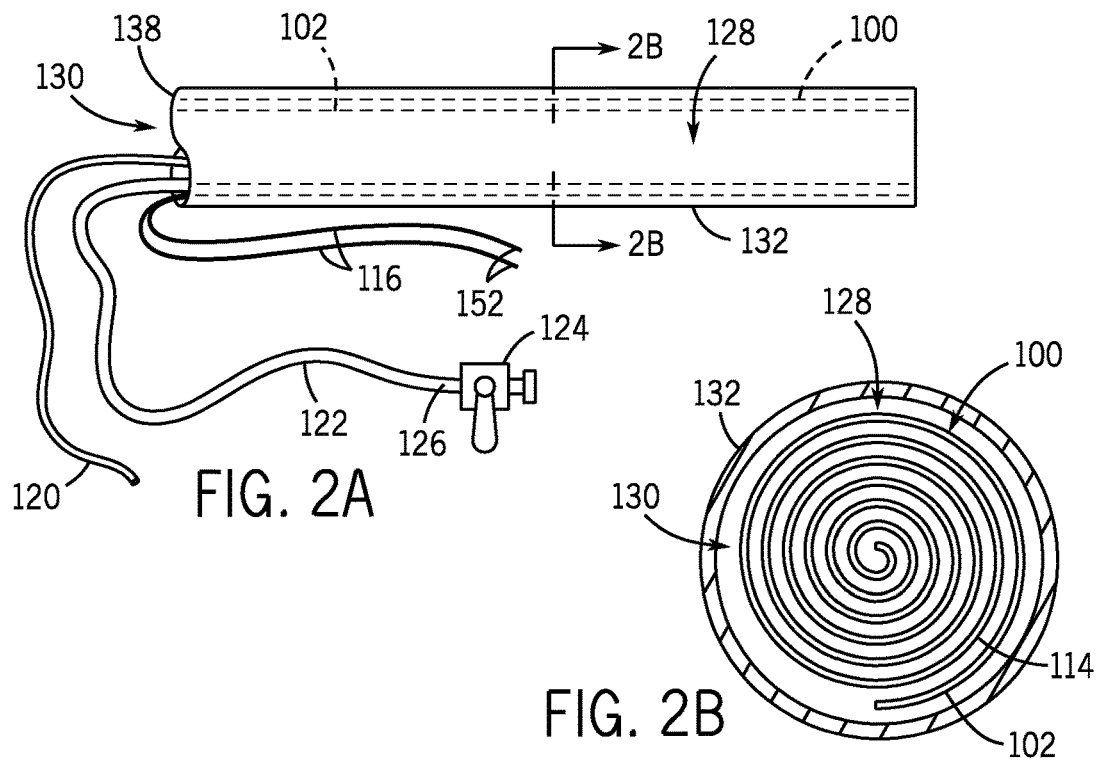
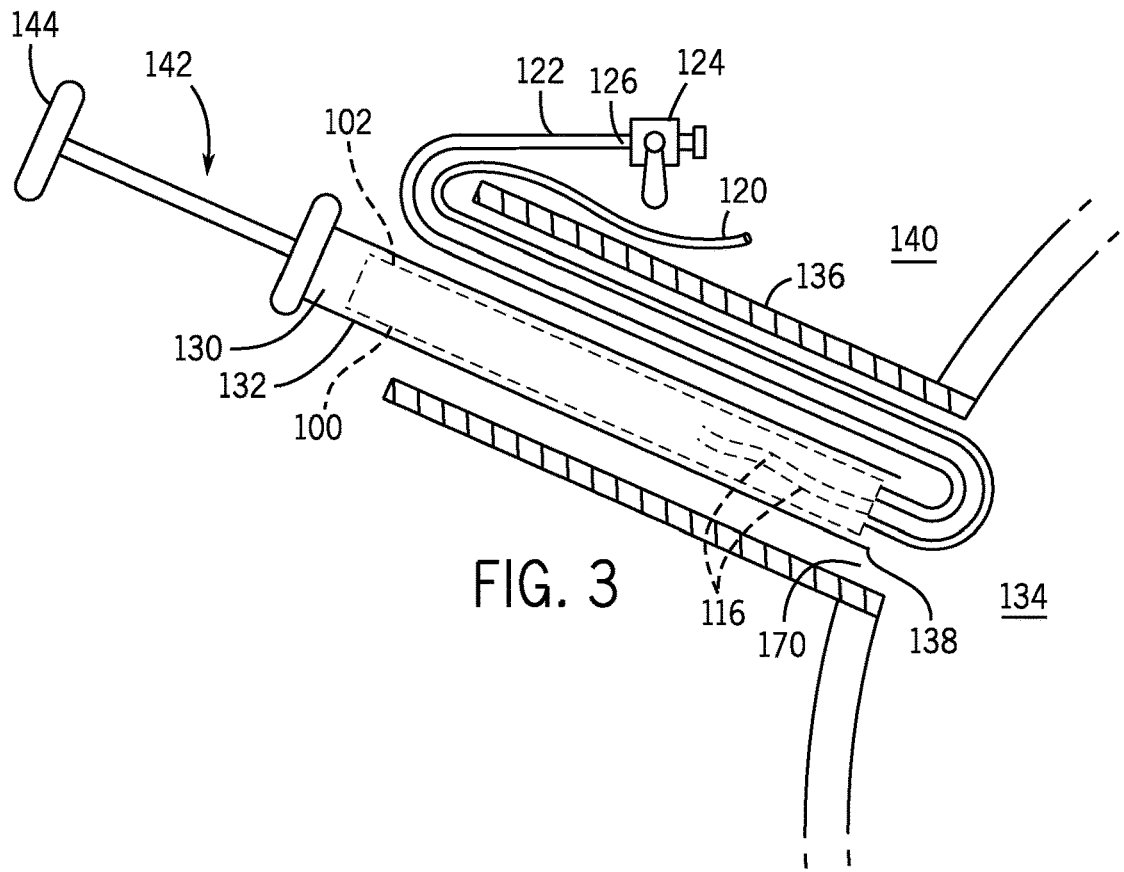

SYSTEM AND METHOD FOR TISSUE RETRIEVAL

CROSS REFERENCE TO RELATED APPLICATIONS

This application is a 371 application of PCT/US2014/06819 filed Dec. 2, 2014, which claims priority from U.S. Provisional Patent Application No. 61/910,878, filed Dec. 2, 2013, and U.S. Provisional Patent Application 61/950,274, filed Mar. 10, 2014, and U.S. Provisional Patent Application 62/018,176, filed Jun. 27, 2014, all of which are incorporated by reference herein for all purposes.

STATEMENT REGARDING FEDERALLY SPONSORED RESEARCH

Not applicable.

FIELD OF THE INVENTION

The present invention relates to a retrieval device for retrieving tissue from a body cavity.

BACKGROUND OF THE INVENTION

Laparoscopy is an increasingly-popular surgical procedure that uses one to five small incisions, each of which is approximately 5-12 millimeters in length and extend down through the abdominal wall to enable access to the abdominal cavity. Each small incision receives a hollow tube or trocar cannula, which act as liners, to hold the incisions open, thereby providing portals into the abdominal cavity. A laparoscopic procedure can then be performed by passing surgical instruments, such as cutting devices, clamps or a viewing apparatus, down the cannulas so that the distal working ends of the instruments can be positioned and used about the surgical site. The proximal handle ends of the instruments remain outside the body where they can be grasped and manipulated by a surgeon or assistant.

In many surgical procedures, it is desirable to excise diseased or unwanted tissues. Once the excised tissue is severed by a snare cauterization technique, for example, it frequently becomes difficult to capture the tissue and retrieve it from the patient. Sometimes the cauterization loop is used in an effort to ensnare the tissue. Other capture techniques involve the use of forceps or the application of suction. However, in using forceps, the forceps naturally tear off a tissue sample from the severed tissue, leaving the main body of the tissue in the patient. In using suction, a vacuum is applied via a suction channel of a suction/irrigation device. The use of suction has the drawback that the suction channel is small, as it must pass through the trocar cannula to enter the abdominal cavity. Thus, the specimen must be reduced into fragments small enough to fit the suction device channel or the specimen will clog the lumen rendering it unusable.

No matter which specific technique is used, the excised tissue frequently escapes from the capturing instrumentality and falls away into the body cavity. Especially in cases where the excised tissue is large, the effort and time expended in retrieving the severed tissue may rival or even exceed the effort and time required to locate and sever the tissue mass. In any event, the manipulations necessary to remove a severed tissue mass generally increase the trauma to the patient, the expense of the surgery and the hospitalization time.

Once the tissue mass is captured, in some situations, the excised tissue is relatively small and can be passed through a suction lumen, however, in other situations the excised tissue is too large to fit through the channel intact. In the latter case, the excised tissue must be cut down into a number of smaller pieces before it can be passed through a cannula. One method of reducing the size of such object is to use a device such as a morcellator, which, in conjunction with a suitable tissue isolation bag, mechanically reduces the size of the tissue mass by a cutting or shearing action. Once the tissue mass has been sufficiently reduced, the isolation bag can then be subsequently withdrawn through the trocar cannula. If such a device is not available, or is ineffective, then the surgeon must increase the size of the abdominal wall incision through which he or she is working, which is undesirable.

Laparoscopic morcellation is a common method of accomplishing the above described task in the operating room. Further, morcellation also allows many surgeries to be performed laparoscopically, reducing recuperation time and providing cosmetic benefits to patients. Laparoscopic morcellation can be used in surgeries such as hysterectomy, cysctectomy, fibroidectomy and myomectomy to remove uteri and uterine fibroids (leiomyomas) through a small abdominal incision. The current standard for the removal of large tissue through a small incision during these surgeries involves grasping tissue and pulling it into a rotating cutting tool operating within the body cavity.

Unfortunately, the above existing approaches have a number of key limitations; 1) they do not provide safe containment of tissue while capturing the severed tissue mass, 2) they do not provide safe containment of tissue during the morcellation process which could lead to seeding (spreading and re-growth) of benign or cancerous tissue and 3) they can lead to accidental damage to surrounding healthy tissue inside the body. In addition to these safety risks, current tissue mass capturing techniques are inefficient because they operate in a piece-wise or serial manner and the procedure time is highly dependent on tumor size, density, and surgeon skill, thereby prolonging operating time.

Therefore, a tissue retrieval device is needed that overcomes the above limitations.

SUMMARY OF THE INVENTION

The present invention relates to a retrieval device for retrieving tissue from a body cavity. The retrieval device includes a pouch having an aperture and a pouch wall defining an interior space. An inflatable rim is coupled to the pouch and facilitates a low profile for insertion into the body and a prominent opening in the pouch for placement of the tissue into the interior space of the pouch. The retrieval device further includes a closure device coupled to the pouch wall for enclosing the tissue within the interior space of the pouch. A portion of the pouch wall may include a self-sealing characteristic that allows an instrument to pierce the pouch wall and the pouch wall to reseal after withdrawal of the instrument. The pouch can move from a retracted position to an expanded position upon inflation of the inflatable rim, which can then be separated by application of a separation force at an area of material weakness in the pouch wall. Additionally, the retrieval device is devoid of additional pouches, retrieval bags, and the like.

Some embodiments of the invention provide a retrieval device for removing tissue. The retrieval device includes a pouch having an aperture and a pouch wall extending therefrom. The pouch has an interior space defined by the pouch wall. In some embodiments, the retrieval device is devoid of additional pouches. The retrieval device also includes an inflatable rim coupled to the aperture of the pouch to facilitate retrieval of the tissue into the interior space of the pouch. A closure device is coupled to the pouch wall for enclosing the tissue within the interior space of the pouch. A portion of the pouch wall includes a self-sealing characteristic which enables the pouch wall to be pierced by an instrument, such that the pouch wall is resealable after withdrawal of the instrument from the pouch wall. In some embodiments, the instrument is a laparoscope configured to pierce the self-sealing characteristic of the pouch wall for visualization of the tissue manipulation within the interior space of the pouch.

In some embodiments, the inflatable rim is releasably coupled to the aperture of the pouch such that the inflatable rim can be separated by application of a separation force at an area of material weakness in the pouch wall. The pouch of the retrieval device may be configured to be folded, rolled or pleated for placement within an insertion device prior to deployment into a patient. In addition, one or more tabs are coupled to an exterior portion of the pouch wall that can be engaged by the instrument to expand the pouch wall from a retracted position to an expanded position. The closure device, in some embodiments, is provided by drawstrings encompassing at least a portion of the pouch wall, such that, upon activation, a force is generated between the tissue and the pouch wall, thereby causing the pouch wall to expand from a retracted position to an expanded position.

The retrieval device may further include an insufflation connector coupled to the inflatable rim. The insufflation connector is configured to insufflate the inflatable rim, thereby providing a rigid rim surrounding the aperture of the pouch. The retrieval device may also include a sealing cap dimensioned to seal the aperture of the pouch. The sealing cap may include an insufflation connector configured to insufflate the interior space of the pouch.

In some embodiments, the pouch is constructed of a transparent material, an opaque material, a ripstop nylon material, a woven nylon material, a polypropylene material, a polyethylene material, a polyester material, a polyvinyl chloride (PVC) material, an ethylene vinyl acetate (EVA) material, thermoplastic elastomers (TPEs), a Kevlar material, or an ultra high molecular weight polyethylene (UHMWPE) material.

Other embodiments of the invention provide a retrieval device for removing tissue. The retrieval device includes a pouch having an aperture and a pouch wall extending therefrom. The pouch has an interior space defined by the pouch wall. The retrieval device also includes an inflatable rim coupled to the aperture of the pouch to facilitate retrieval of the tissue into the interior space of the pouch. A closure device is coupled to the pouch wall for enclosing the tissue within the interior space of the pouch, and the pouch is configured to move from a retracted position to an expanded position upon inflation of the inflatable rim.

Some embodiments of the invention provide a retrieval device for removing tissue. The retrieval device includes a pouch having an aperture and a pouch wall extending therefrom. The pouch has an interior space defined by the pouch wall. The retrieval device also includes an inflatable rim or inflation port releasably coupled to the aperture of the pouch to facilitate retrieval of the tissue into the interior space of the pouch. A closure device is coupled to the pouch wall for enclosing the tissue within the interior space of the pouch. The inflatable rim can be separated by application of a separation force at an area of material weakness in the pouch wall.

Some embodiments of the invention provide a retrieval device for removing tissue. The retrieval device includes a pouch having an aperture and a pouch wall extending therefrom. The pouch has an interior space defined by the pouch wall. The retrieval device also includes an inflatable rim coupled to the aperture of the pouch to facilitate retrieval of the tissue into the interior space of the pouch. A closure device is coupled to the pouch wall for enclosing the tissue within the interior space of the pouch. One or more operating sleeves or access port sleeves may be coupled to the pouch wall and configured to receive an instrument for manipulation of the tissue or a visualization device such as a laparoscope.

Other embodiments of the invention provide a retrieval device for removing tissue. The retrieval device includes a pouch including an aperture and a pouch wall extending therefrom. The pouch has an interior space defined by the pouch wall. A handle is coupled adjacent the aperture of the pouch to facilitate retrieval of the tissue into the interior space of the pouch. A closure device is coupled to the pouch wall for enclosing the tissue within the interior space of the pouch. One or more access port sleeves are coupled to the pouch wall and configured to receive an instrument for manipulation of the tissue.

In one embodiment, the closure device includes a valve activated by a deployment mechanism coupled to the handle of the retrieval device, and a pliable ring integrated into the pouch wall configured to open the aperture of the pouch.

Still other embodiments of the invention provide a retrieval device for removing tissue. The retrieval device includes a pouch including an aperture and a pouch wall extending therefrom, the pouch having an interior space defined by the pouch wall; a closure device for enclosing the tissue within the interior space of the pouch and/or closing an open end of the access port sleeve; and an access port sleeve coupled to the pouch wall and configured to receive an instrument for manipulation or visualization of the tissue. The retrieval device may include drawstrings for unfolding the access port sleeve from a collapsed state to an expanded state. The drawstrings can have the ability to seal the access port sleeve. The retrieval device may include a seal between the access port sleeve and the interior space of the pouch. The retrieval device may include one or more additional access port sleeves coupled to the pouch wall and configured to receive an instrument for manipulation or visualization of the tissue. The closure device can be a heat sealer. The closure device can comprise a loop at an end of an elongated element in which a knot slides on the elongated element to make the loop collapsible.

In another embodiment, the invention provides a method for retrieval of a tissue specimen using a tissue retrieval device. The method involves providing a pouch including an aperture and a closure device attached thereto, and providing an inflatable rim or inflation port releasably coupled to the aperture of the pouch to facilitate retrieval of the tissue specimen into the pouch. The pouch is inserted into a patient and the tissue specimen is inserted through the inflatable rim into the aperture of the pouch. The closure device is activated to cause the pouch to move from a retracted position to an extended position. The inflatable rim is detached, upon deflation, from the pouch. The pouch and enclosed tissue specimen are removed from the patient.

Some embodiments of the invention provide a method for retrieval of a tissue specimen using a tissue retrieval device.

The method involves providing a pouch including an aperture and a closure device attached thereto, and providing an inflatable rim coupled to the aperture of the pouch to facilitate retrieval of the tissue specimen into the pouch. The pouch is inserted into a patient and the tissue specimen is inserted through the inflatable rim into the aperture of the pouch. The closure device is activated to cause the pouch to move from a retracted position to an extended position. The pouch and enclosed tissue specimen are removed from the patient.

In yet another embodiment, a method for retrieval of a tissue specimen using a tissue retrieval device is provided. The method involves inserting a pouch into a patient. The pouch includes an aperture and a closure device attached thereto. The pouch further includes an inflatable rim coupled to the aperture of the pouch to facilitate retrieval of the tissue specimen into the pouch. The tissue specimen is inserted through the inflatable rim into the aperture of the pouch. The closure device is activated to cause the pouch to move from an extended position to a retracted position. One or more operating sleeves are extended from the tissue retrieval device, and a visualization device or an assisting device is inserted through the operating sleeve into the pouch. The pouch and enclosed tissue specimen are then removed from the patient.

In still another embodiment, a method for retrieval of a tissue specimen using a tissue retrieval device is provided. The method involves inserting a pouch into a patient, the pouch including an aperture; inserting the tissue specimen into the aperture of the pouch; extending one or more operating sleeves from the tissue retrieval device; inserting at least one of a visualization device and an assisting device through at least one operating sleeve into the pouch; and removing the pouch and enclosed tissue specimen from the patient. In the method, an opening can be created by cutting open a sealed passage of each operating sleeve after extending the operating sleeve from the tissue retrieval device. In the method, an open end of the operating sleeve can be closed with a closure device. The closure device can be a heat sealer. The closure device can comprise a loop at an end of an elongated element in which a knot slides on the elongated element to make the loop collapsible.

These and other features, aspects, and advantages of the present invention will become better understood upon consideration of the following detailed description, drawings, and appended claims.

BRIEF DESCRIPTION OF THE DRAWINGS

FIG. 2A is side view of the tissue retrieval device of FIG. 1 in a retracted position surrounded by a hollow tube.

FIG. 2B is a cross-sectional view of the tissue retrieval device in the retracted position surrounded by the hollow tube taken along line 2B-2B of FIG. 2A.

FIG. 3 is a side view of an insertion device for the tissue retrieval device.

DETAILED DESCRIPTION OF THE INVENTION

Figure 1:
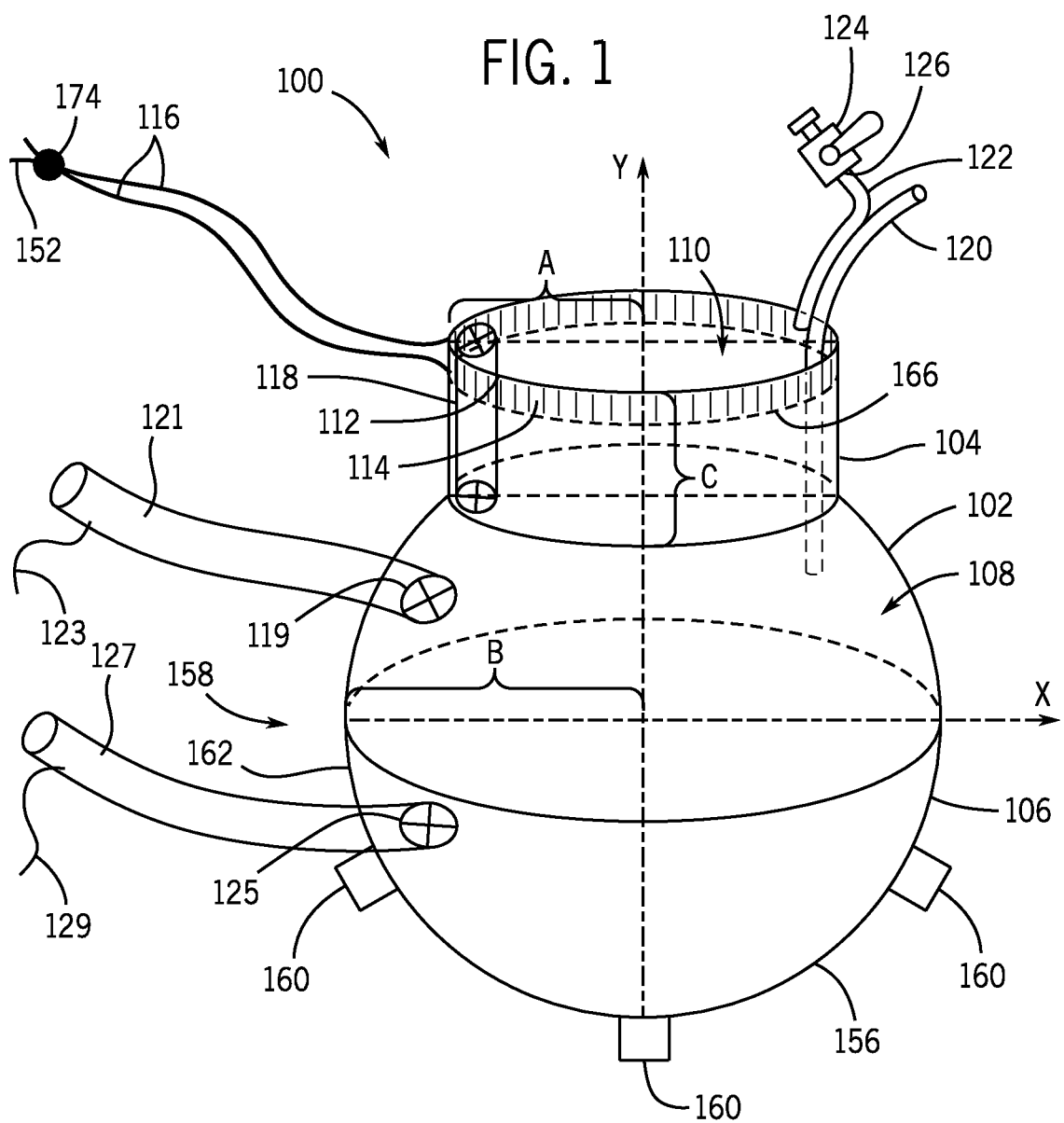
FIG. 1 is a perspective view of an example tissue retrieval device according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

FIG. 1 illustrates an example retrieval device 100 for laparoscopic specimen retrieval. The retrieval device 100 is formed by a pouch 102 having a neck portion 104 and a pouch wall 106 downwardly extending therefrom. An interior space 108 is defined by the pouch wall 106 for receiving tissue masses (not shown). The pouch 102 includes an aperture 110 that circumscribes a perimeter 112 of the neck portion 104 and creates an opening for placement of the tissue masses within the interior space 108 of the pouch 102. An inflatable rim 114 is coupled to the perimeter 112 of the neck portion 104 adjacent the pouch aperture 110. When insufflated, the inflatable rim 114 provides rigidity to the rim and facilitates retrieval of the tissue specimens into the pouch 102, as will be described in further detail below. Once the tissue specimens are retrieved into the retrieval device 100, a drawstring-like closure device 116 coupled to the neck portion 104 of the pouch wall 106 is activated to enclose the tissue specimens within the interior space 108 of the pouch 102 to prevent seeding, which may occur when tissue spills into the body of the patient.

The pouch 102 has the drawstring-like closure device 116 threaded through the perimeter 112 of the pouch wall 106. The pouch 102 is substantially spherical in shape and can be constructed from a nylon (e.g., ripstop nylon or a woven nylon) or polyvinyl chloride (PVC) material to help prevent any tearing that might occur during surgery, however any suitable material (e.g., a polypropylene material, a polyethylene material, a polyester material, an ethylene vinyl acetate (EVA) material, thermoplastic elastomers (TPEs), a Kevlar material, or an ultra-high molecular weight polyethylene (UHMWPE) material) can be used as an alternative. In some embodiments, the pouch 102 may be constructed from a transparent material, such that when a laparoscope is introduced into the abdominal cavity of the patient outside of the pouch 102, the surgery can be visualized through the transparent material. In other embodiments, the pouch 102 may be constructed from an opaque material.

Alternatively, the pouch 102 may include one or more laparoscope ports 118 disposed on the neck portion 104 of the pouch wall 106. The laparoscope port 118 may be substantially cylindrical in shape and extend through the aperture 110 of the pouch 102. The laparoscope port 118 may be configured to receive a laparoscope (not shown) for visualization into the interior space 108 of the pouch 102 so that the surgical specimen can then be removed with a tissue morcellator under direct visualization. The laparoscope port 118 may also have a self-sealing characteristic that enables the laparoscope port 118 to be pierced by an instrument, such as a laparoscope, and resealed after withdrawal of the instrument from the laparoscope port 118.

Additionally, or alternatively, the pouch 102 may include one or more access ports disposed on the pouch wall 106 to provide laparoscope visualization into the pouch 102. As shown in FIG. 1, an upper access port 119 is provided on the pouch wall 106. An operating sleeve or upper access port sleeve 121 may be coupled to the upper access port 119 and extend outwardly from the pouch wall 106. In addition, a tether 123 may be coupled to the access port sleeve 121 to allow an instrument, such as a grasper, to pull the access port sleeve 121 through an abdominal wall incision. Once the access port sleeve 121 is pulled through the incision, the access port sleeve 121 may be configured to receive an instrument, such as a laparoscope or tissue manipulation instrument, for visualization and manipulation of the specimen within the interior space 108 of the pouch 102. The access port 119 may have a self-sealing characteristic that enables the pouch wall 106 to be pierced by an instrument, such as a laparoscope, and resealed after withdrawal of the instrument from the access port 119.

Similar to the upper access port 119 and access port sleeve 121, the pouch 102 may include a lower access port 125 disposed on the pouch wall 106 and a lower access port sleeve 127 that extends outwardly from the pouch wall 106. In addition, a tether 129 may be coupled to the access port sleeve 127 to allow an instrument, such as a grasper, to pull the access port sleeve 127 through an abdominal wall incision. Once the access port sleeve 127 is pulled through the incision, the access port sleeve 127 may be configured to receive an instrument, such as a laparoscope or tissue manipulation instrument, for visualization and manipulation of the specimen within the interior space 108 of the pouch 102. The access port 125 may also have a self-sealing characteristic that enables the pouch wall 106 to be pierced by an instrument, such as a laparoscope, and resealed after withdrawal of the instrument from the access port 125.

Still referring to FIG. 1, the aperture 110 of the pouch 102, which is substantially cylindrical in shape, may have a radius A of about 5 centimeters, as measured along a horizontal axis X. Similarly, the interior space 108 defined by the pouch wall 106 may have a radius B of about 10 centimeters, as measured along the horizontal axis X. The neck portion 104, which extends upwardly from the pouch wall 106 along a vertical axis Y, may have a height C of about 8 centimeters. However, it is contemplated that the pouch 102 may have other dimensions and is not limited to the dimensions described above.

The retrieval device 100 can further include an insufflation port 120 that is connected to an insufflator (not shown) and extends through the aperture 110 and into the interior space 108 of the pouch. The insufflation port 120 may provide a non-flammable gas, such as carbon dioxide ($CO_2$), into the interior space 108 to insufflate the pouch 102 for visualization during the surgery. Similarly, an inflation port 122 may be connected to the inflatable rim 114 for inflation purposes. In some embodiments, the inflation port 122 may be releasably coupled to the inflatable rim 114. A control valve 124 may be coupled to an end portion 126 of the inflation port 122, such that when the inflatable rim 114 is inflated to a desired pressure, the control valve 124 may be closed to prevent the rim 114 from deflating.

Turning now to FIGS. 2A-9, the retrieval device 100 is intended to be used during surgery after tissue has been resected in order to remove specimens from the abdomen. The retrieval device 100 is introduced into the abdomen prior to the start of the procedure. The abdomen may be insufflated, or essentially blown up like a balloon, with carbon dioxide gas. This elevates the abdominal wall above the internal organs like a dome to create a working and viewing space. $CO_2$ is used because it is common to the human body and can be absorbed by tissue and removed by the respiratory system. $CO_2$ is also non-flammable, which is important because electrosurgical devices are commonly used in laparoscopic procedures.

Prior to beginning the laparoscopic procedure, the inflatable rim 114 of the retrieval device 100 may be provided in a retracted position 128, as shown in FIGS. 2A and 2B, and placed into an inner space 130 of a hollow shaft 132. In the retracted position 128, the inflatable rim 114 of the pouch 102 may be rolled-up about the vertical axis Y shown in FIG. 1, and placed inside the hollow shaft 132 for insertion into an abdominal cavity 134 of a patient. The inner space 130 of the hollow shaft 132 can be partially hollow, such that the hollow shaft 132 is dimensioned to surround a portion of the pouch 102. The inner space 130 of the hollow shaft 132 is where the pouch 102 is placed prior to deploying into the abdominal cavity 134 of a patient, as shown in FIG. 3. The hollow shaft 132 is cylindrical in shape and can be between 12-15 centimeters in length. The hollow shaft 132 can be constructed of stainless steel or polymeric tubing and the hollow shaft 132 can have an outer diameter that is smaller than the diameter of a trocar cannula 136, as shown in cross-section in FIG. 3. An end portion 138 of the hollow shaft 132 can be chamfered, flared or lubricated to assist deployment of the retrieval device 100 into the abdominal cavity 134.

As shown in FIG. 2A, the drawstring-like closure device 116, the insufflation port 120 and the inflation port 122 remain exterior to the inner space 130 of the hollow shaft 132 and are not rolled up with the pouch 192 in the retracted position 128. Thus, once the pouch 102 is inserted into the abdominal cavity 134, the insufflation port 120 and the inflation port 122 remain in an external environment 140 outside the patient so the inflatable rim 114 and pouch 102, respectively, can be inflated in the abdominal cavity 134, as will be described in further detail below.

Turning now to FIG. 3, an insertion device 142 can be used to deploy the retrieval device 100 into the abdominal cavity 134. To begin, the retrieval device 100, which is in the retracted position 128, and the hollow shaft 132 are coaxially positioned inside the insertion device 142. A handle 144 of the insertion device 142 is then pushed in until the retrieval device 100 is deployed into the abdominal cavity 134. Once deployed, the insertion device 142 and hollow shaft 132 are removed from the trocar cannula 136.

Figure 4A:
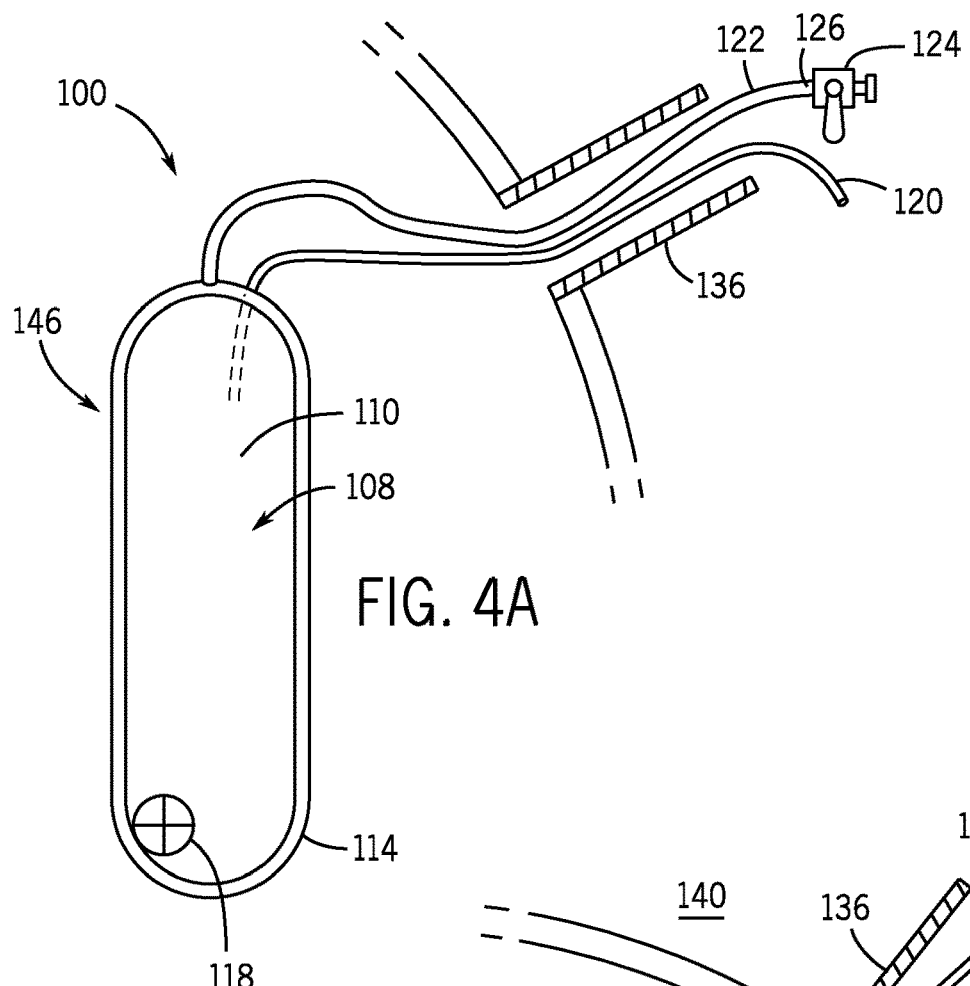
FIG. 4A is a top view of the tissue retrieval device deployed from the insertion device of FIG. 3.
Figure 4B:
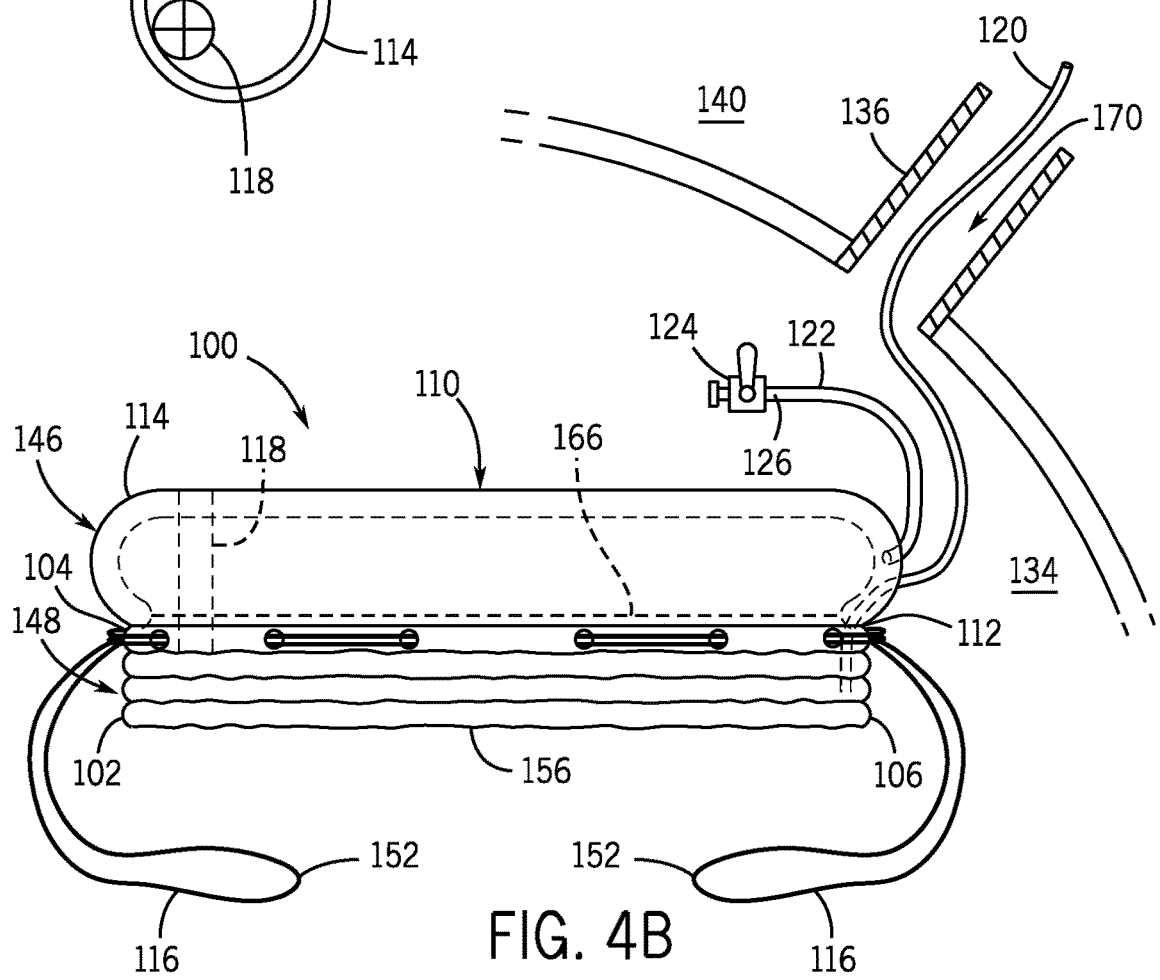
FIG. 4B is a side view of the tissue retrieval device with a pouch in a retracted position and an inflatable rim insufflated.

Turning now to FIGS. 4A and 4B, once the retrieval device 100 is introduced into the abdominal cavity 134 via the trocar cannula 136 port, the inflatable rim 114 is inflated using the inflation port 122 connected to a laparoscopic insufflator (not shown). As the inflatable rim 114 is inflated with $CO_2$ from the laparoscopic insufflator, the rim 114 unrolls from the retracted position 128 to an inflated, extended position 146. As best shown in FIG. 4B, the pouch 102 remains in a retracted position 148 as the inflatable rim 114 is inflated. Thus, the pouch 102 of the retrieval device 100 can be a pleated or rolled material as necessary to make an expandable configuration. As such, the inflatable rim 114 in the inflated, extended position 146 and the pouch 102 in the retracted position 148 provides a raft like structure that may be used as a tissue collection site.

Figure 5:
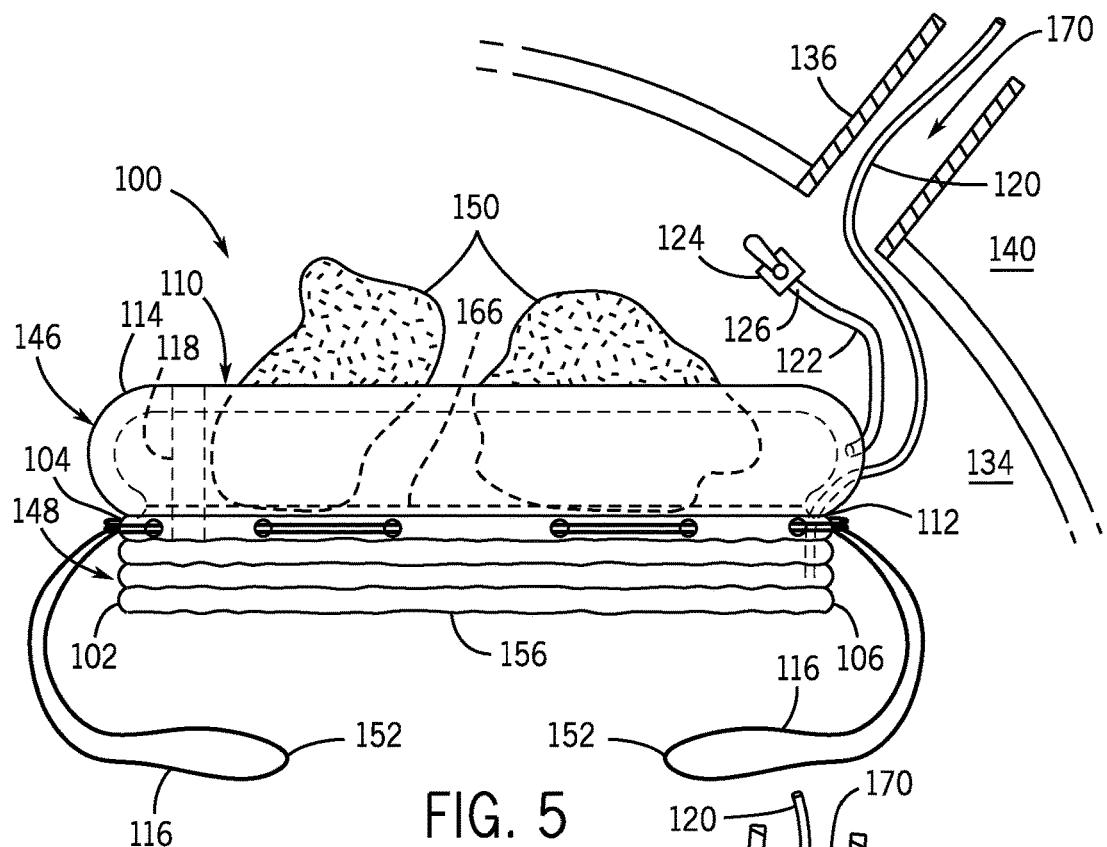
FIG. 5 is a side view of the tissue retrieval device of FIG. 4B surrounding tissue specimens within an abdominal cavity of a patient.
Figure 6:
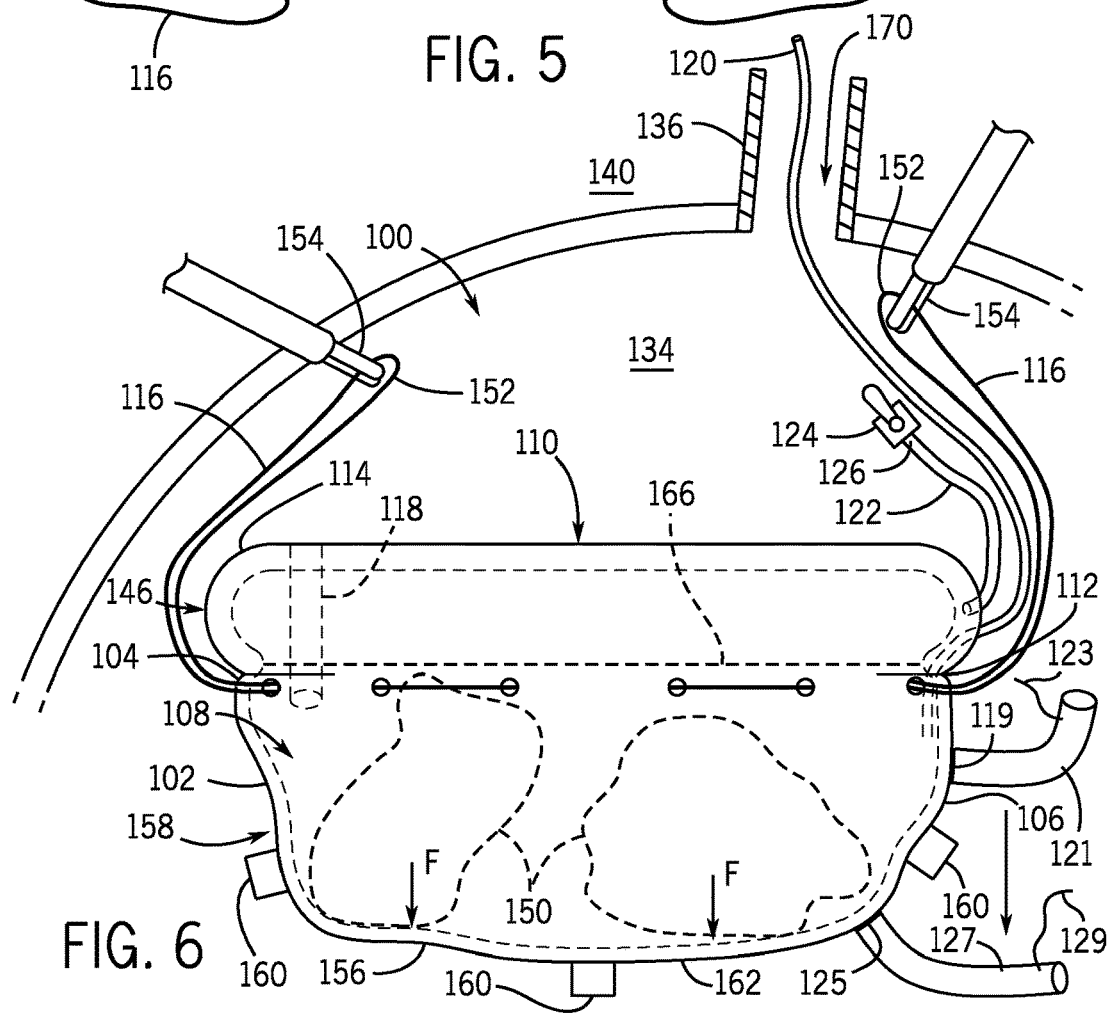
FIG. 6 is a side view of the tissue retrieval device with the pouch in an expanded position upon activation of a closure device.

Once the inflatable rim 114 is inflated to the desired pressure, the control valve 124 can be closed and pushed into the abdominal cavity 134, as shown in FIG. 5. Tissue specimens 150 may then be placed into the retrieval device 100 using a grasping instrument (not shown) inserted through the trocar cannula 136. When the procedure is completed (i.e., the tissue specimens 150 have been retrieved), end portions 152 of the drawstring-like closure device 116 can be grasped and pulled upward using one or more grasping instruments 154, as shown in FIG. 6. Pulling the end portions 152 of the drawstring-like closure device 116 that encompasses a portion of the pouch wall 106, causes the tissue specimens 150 to generate downward forces F on a bottom portion 156 of the pouch 102. Thus the downward forces F cause the pouch wall 106 to expand from the retracted position 148, as shown in FIG. 5, to an extended position 158 thereby forming the pouch 102, as shown in FIG. 6.

In some instances, however, the downward forces F generated by the tissue specimens 150 (e.g., due to smaller tissue masses) are not sufficient to expand the pouch wall 106 from the retracted position 148 to the fully extended position 158. Therefore, in some embodiments, a plurality of tabs 160 are disposed on an exterior portion 162 of the pouch wall 106 for the grasping instruments 154 to engage. As such, the grasping instruments 154, as shown in FIG. 6, may grasp the necessary tabs 160 to expand the pouch wall 106 to the fully extended position 158.

Figure 7:
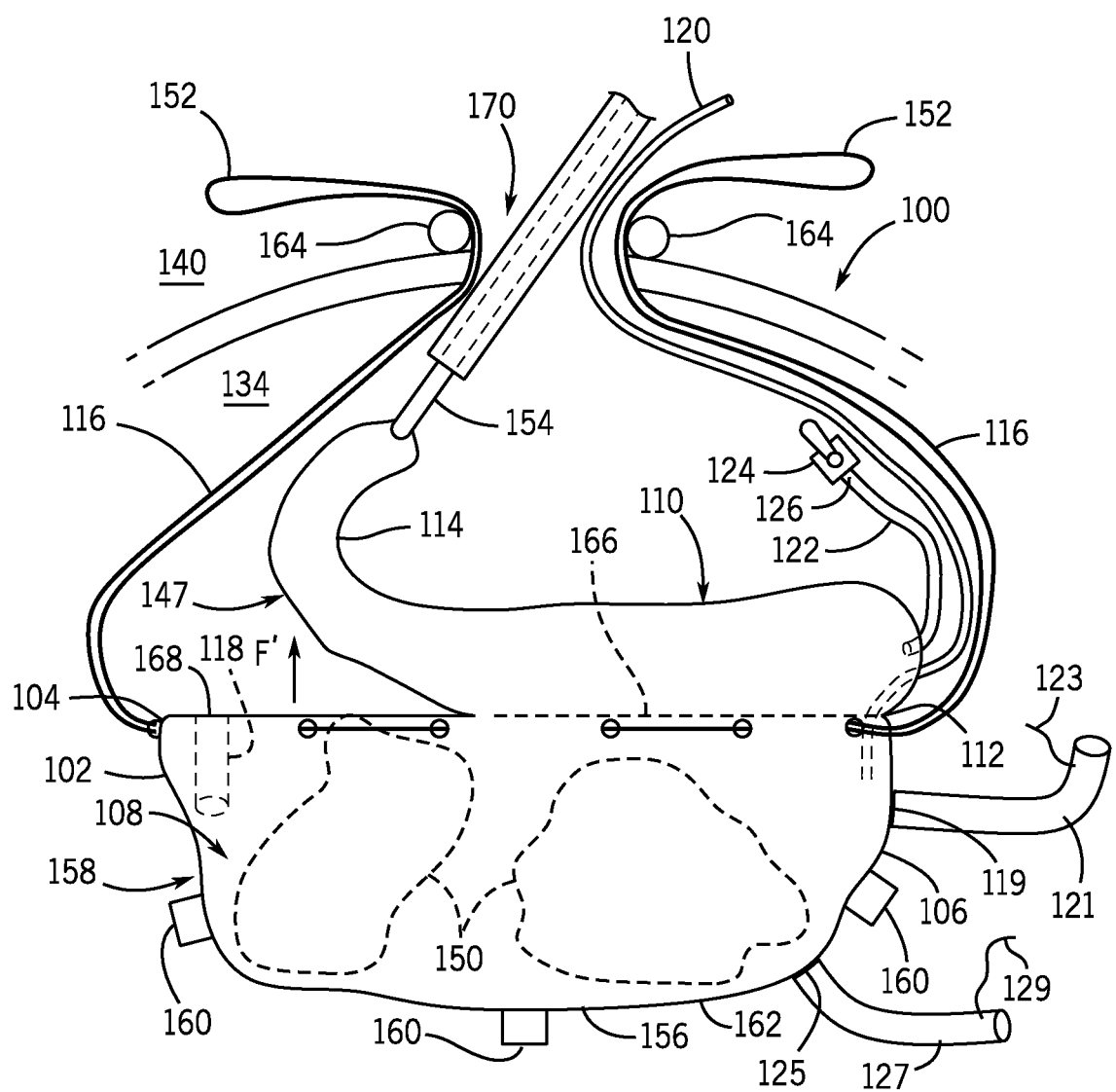
FIG. 7 is a side view of the tissue retrieval device of FIG. 6 and an instrument being used to deflate and detach the inflatable rim from the pouch.

Turning now to FIG. 7, once the pouch 102 has been stretched into the extended position 158, in some embodiments, a stabilizing ring 164 may be provided in place of the trocar cannula 136 to provide better instrument manipulation within the retrieval device 100. Once the trocar cannula 136 is removed from the abdominal cavity 134, the inflatable rim 114 may be punctured and deflated into a retracted position 147 using any suitable instrument to puncture the material of the inflatable rim 114. The grasping instrument 154 may then be manipulated by a user to grasp a portion of the inflatable rim 114 and detach the inflatable rim 114 from the pouch 102.

In some embodiments, an area of material weakness 166 may be provided between the pouch 102 and the inflatable rim 114, as shown in FIG. 7. Thus, as an upwardly separation force F' is applied to the inflatable rim 114 using the grasping instrument 154, the inflatable rim 114 can be separated from the pouch 102 along the area of material weakness 166. The area of material weakness 166 may be provided in the form of a perforation, for example, that is parallel to a top edge 168 of the pouch 102. The perforation allows the inflatable rim 114 to be separated from the pouch 102 by a tearing action that generates the separation force F'. The inflatable rim 114 can then be removed from the abdominal cavity 134 through an abdominal wall entry port 170. However, in some embodiments, the inflatable rim 114 is deflated and remains coupled to the pouch 102, while the inflation port 122 is removed from the abdominal cavity 134.

Figure 8:
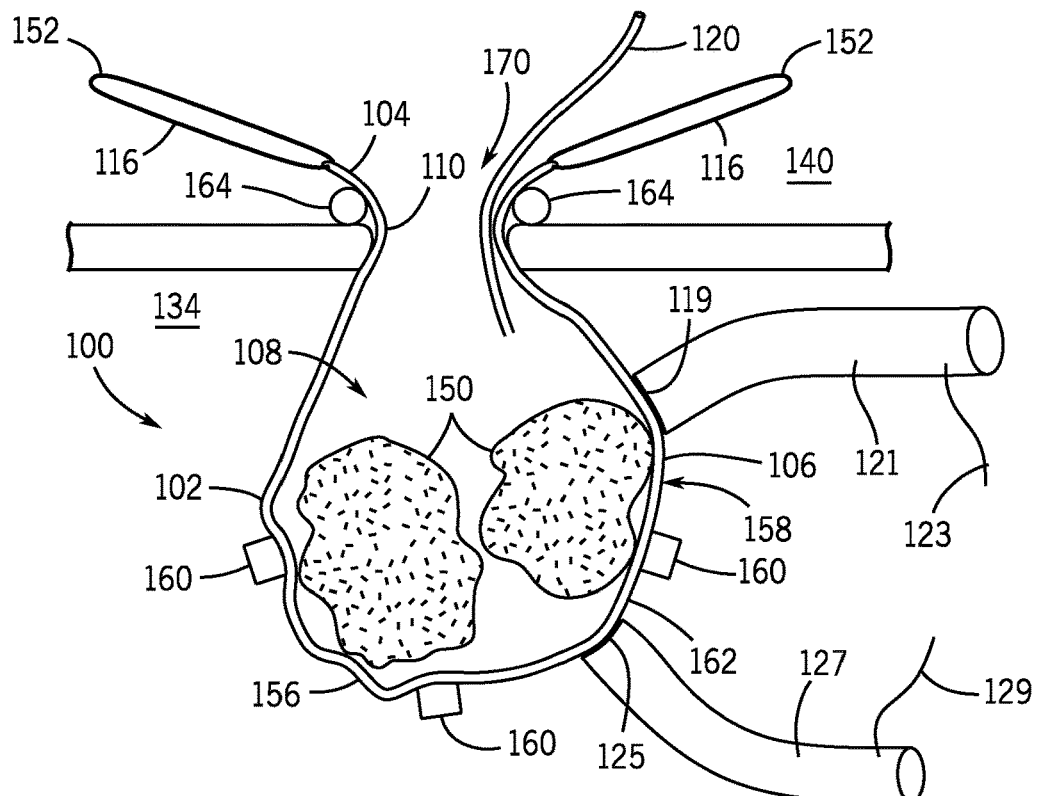
FIG. 8 is a side view of the tissue retrieval device of FIG. 7 after removal of the inflatable rim from the pouch.
Figure 9:
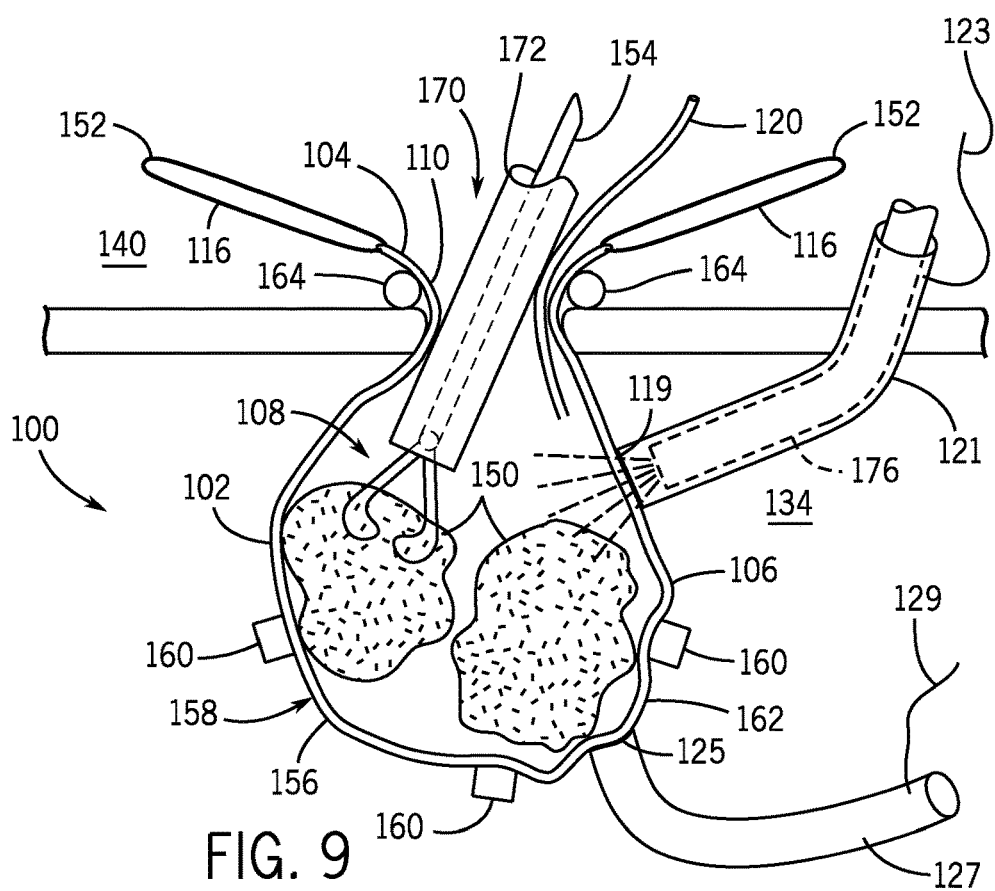
FIG. 9 is a side view of the tissue retrieval device of FIG. 8 and an instrument being used to morcellate the tissue specimens for removal from the abdominal cavity.

Turning now to FIG. 8, once the inflatable rim 114 is removed from the abdominal cavity 134, the end portions 152 of the drawstring-like closure device 116 and the neck portion 104 of the pouch 102 may be exteriorized from the abdominal cavity 134. By exteriorizing the end portions 152 and the neck portion 104, the interior space 108 of the pouch 102 is sealed from the abdominal cavity 134 to inhibit portions of the tissue 150 from entering the abdominal cavity 134 during the morcellation process. Because the tissue 150 may be too large to fit through the abdominal wall entry port 170, a morcellator 172 and grasping instrument 154 may be introduced into the pouch 102 to reduce the tissue volume, as shown in FIG. 9. The morcellator 172 may be any suitable, commercially available tissue morcellator.

Once the morcellator 172 and the grasping instrument 154 are introduced through the neck portion 104 to the interior space 108 of the pouch 102, as shown in FIG. 9, the neck portion 104 may be cinched down around the morcellator 172 shaft using a closure lock 174 (see FIG. 1) coupled to the drawstring-like closure device 116. The pouch 102 may then be insufflated with $CO_2$ through the insufflation port 120 to provide better visualization. A laparoscope 176 may be inserted through the upper access port sleeve 121 to visualize manipulation of the tissue 150 within the pouch 102. Alternatively, the laparoscope 176 could be inserted through the lower access port sleeve 127 to provide visualization into the pouch 102, or the laparoscope 176 may be inserted through the abdominal wall entry port 170 for visualization of the tissue specimens 150 to be removed with the tissue morcellator 172 under direct visualization. In yet another alternative, the laparoscope 176 can be introduced into the abdominal cavity 134 outside the retrieval device 100 and the process can be visualized through the clear pouch 102. After the tissue 150 is morcellated using the morcellator 172, the pouch 102 and morcellated tissue (not shown) can be removed from the abdominal cavity 134 through the abdominal wall entry port 170.

Figure 10A:
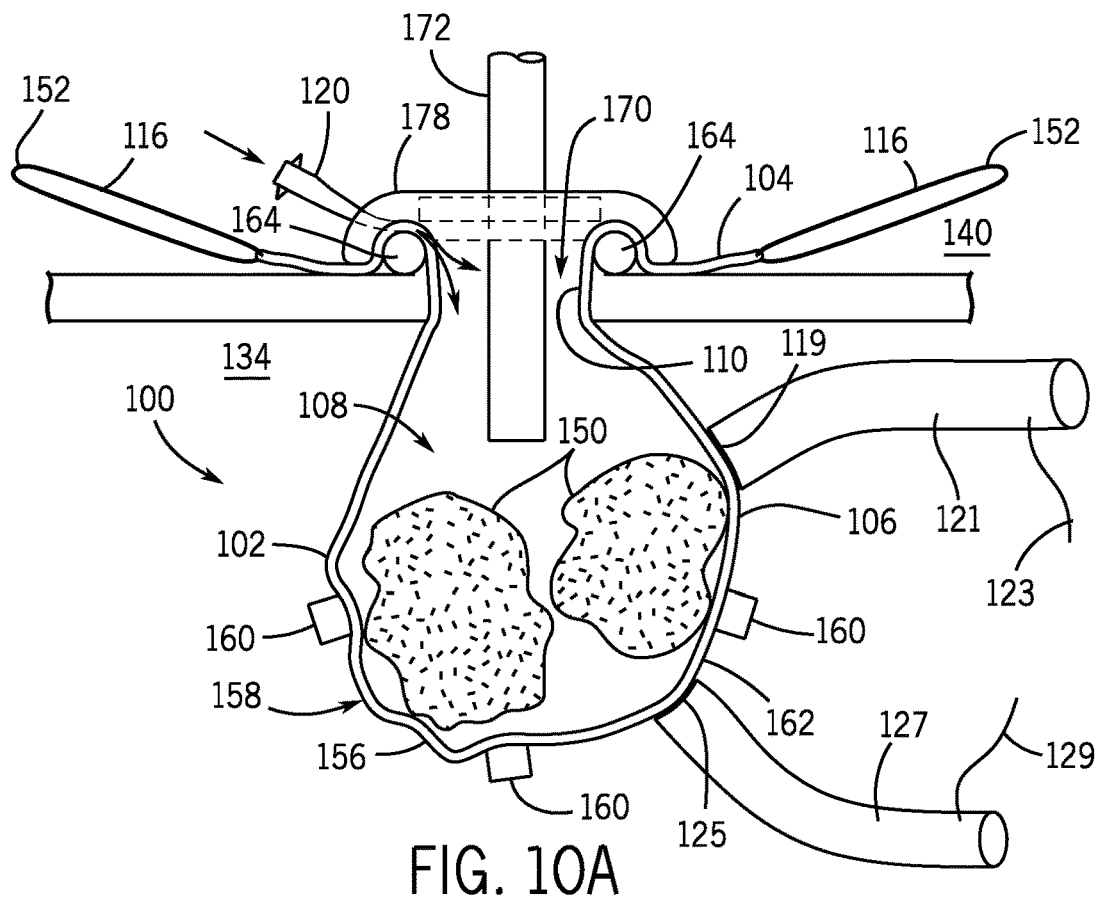
FIG. 10A is a side view a sealing cap attached to the tissue retrieval device prior to insufflation of the pouch through an insufflation port.
Figure 10B:
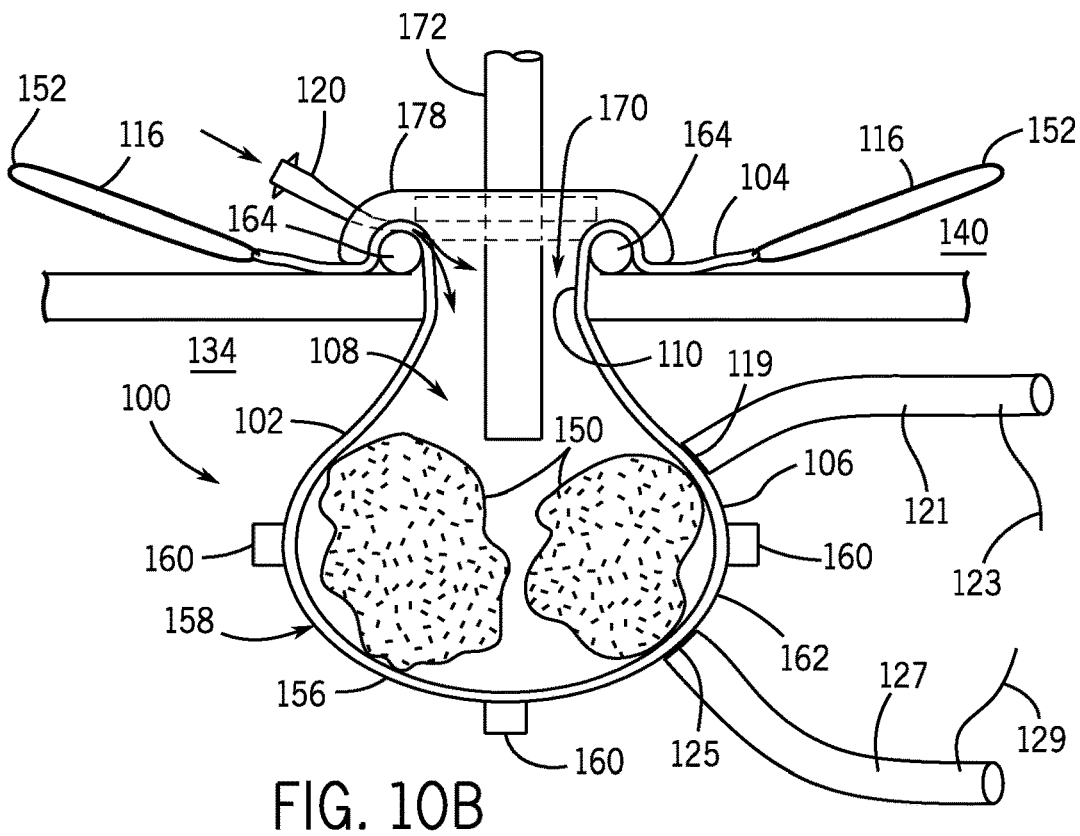
FIG. 10B is a side view the sealing cap of FIG. 10A attached to the tissue retrieval device after insufflation of the pouch.

If necessary, a seal cap 178 may be provided prior to morcellation of the tissue 150, as shown in FIGS. 10A and 10B, to seal the abdominal wall entry port 170. The seal cap 178 may be placed onto the neck portion 104 of the pouch wall 106 and may be dimensioned to receive the stabilizing ring 164 to create the seal at the entry port 170, as shown in FIG. 10A. The seal cap 178 enables the pouch 102 to be distended, as shown in FIG. 10B, using $CO_2$ from the insufflation port 120 to provide an airtight pouch 102. The airtight pouch 102 may help avoid contamination in the abdominal cavity 134 from fluid and the tissue 150.

The airtight pouch 102 may be necessary during certain types of surgery, such as adnexal surgery. For example, when dealing with an ovarian cyst, the surgeon inserts the pouch 102 in the abdominal cavity 134, puts the ovary in the pouch 102 and then closes the seal cap 178. The pouch 102 is then insufflated to the extended position 158 via the insufflation port 120. As previously described, the pouch 102 may have a laparoscope port 118 and/or access ports 119, 125 incorporated into it that allow for punctures from various surgical instruments (e.g., camera, laparoscope, grasping instruments) into the pouch 102. Thus, the ovarian surgery can be performed inside the pouch 102 which avoids spillage from an ovarian cyst into the peritoneal cavity. Ovarian cysts can have premalignant or malignant changes that are not detected preoperatively and by performing the surgery in a contained environment, there is not spillage of contents into the abdominal cavity 134. Once the cyst has been removed from the ovary and the ovary repaired, the pouch 102 can be closed and withdrawn with the tissue specimen or alternatively, a standard endobag can be placed into the pouch 102 to catch the ovarian cyst and this can then be sent for a frozen section if indicated.

Figure 11:
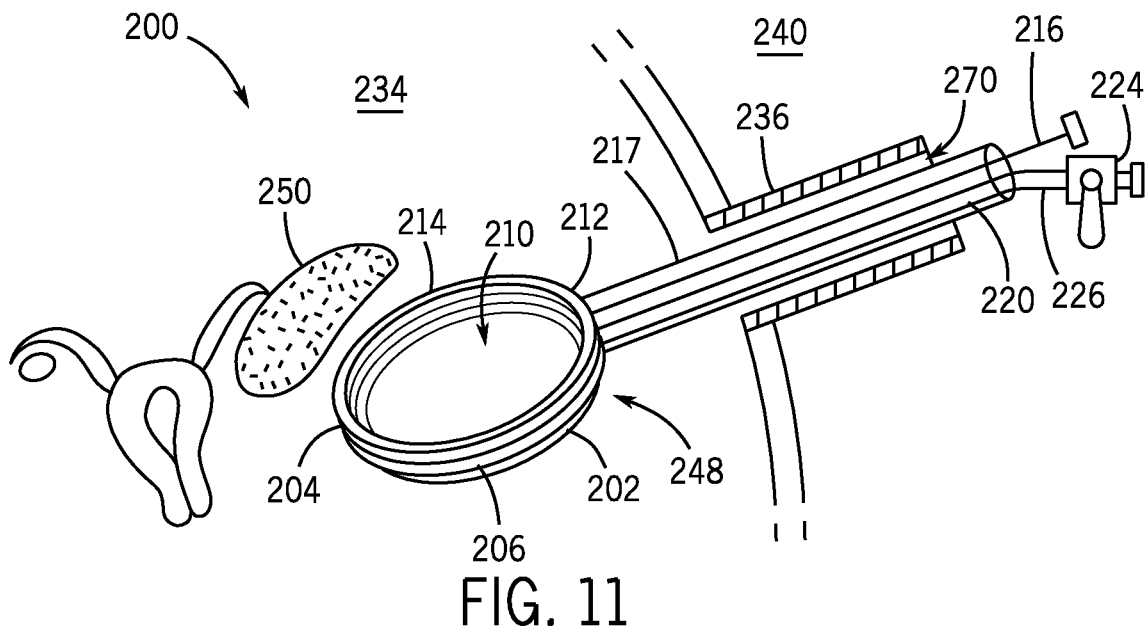
FIG. 11 is a side perspective view of a tissue retrieval device with a pouch in a retracted position.
Figure 12:
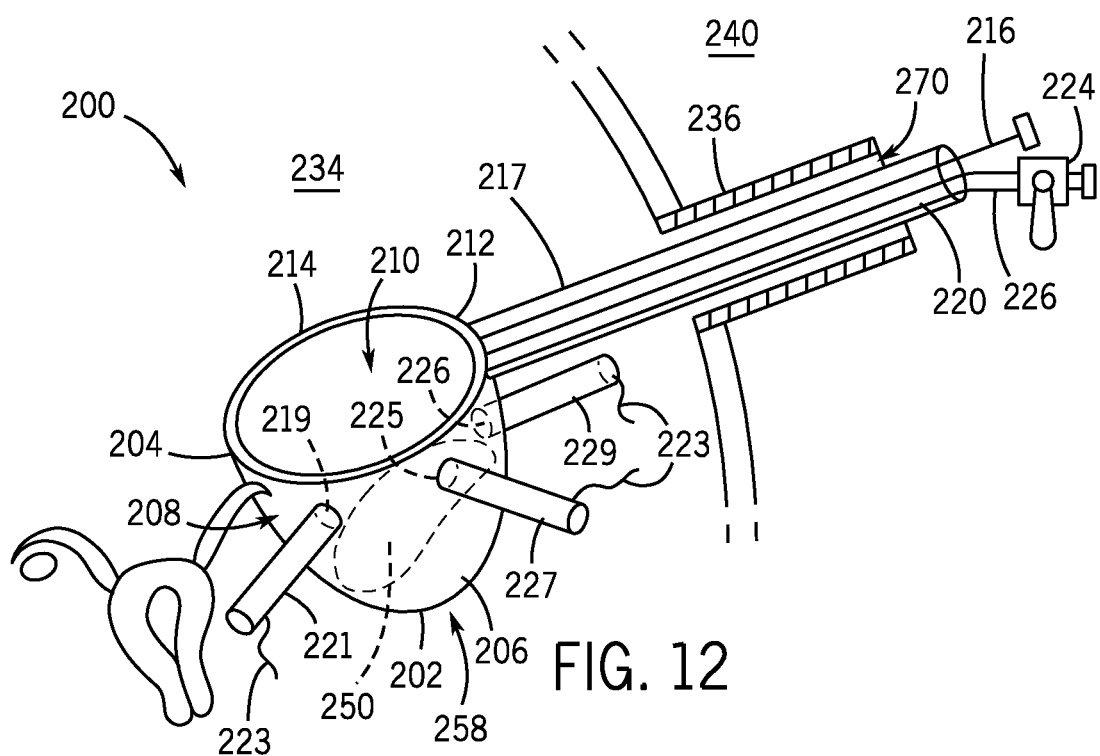
FIG. 12 is a side perspective view of the tissue retrieval device of FIG. 11 with the pouch in an expanded position.
Figure 13:
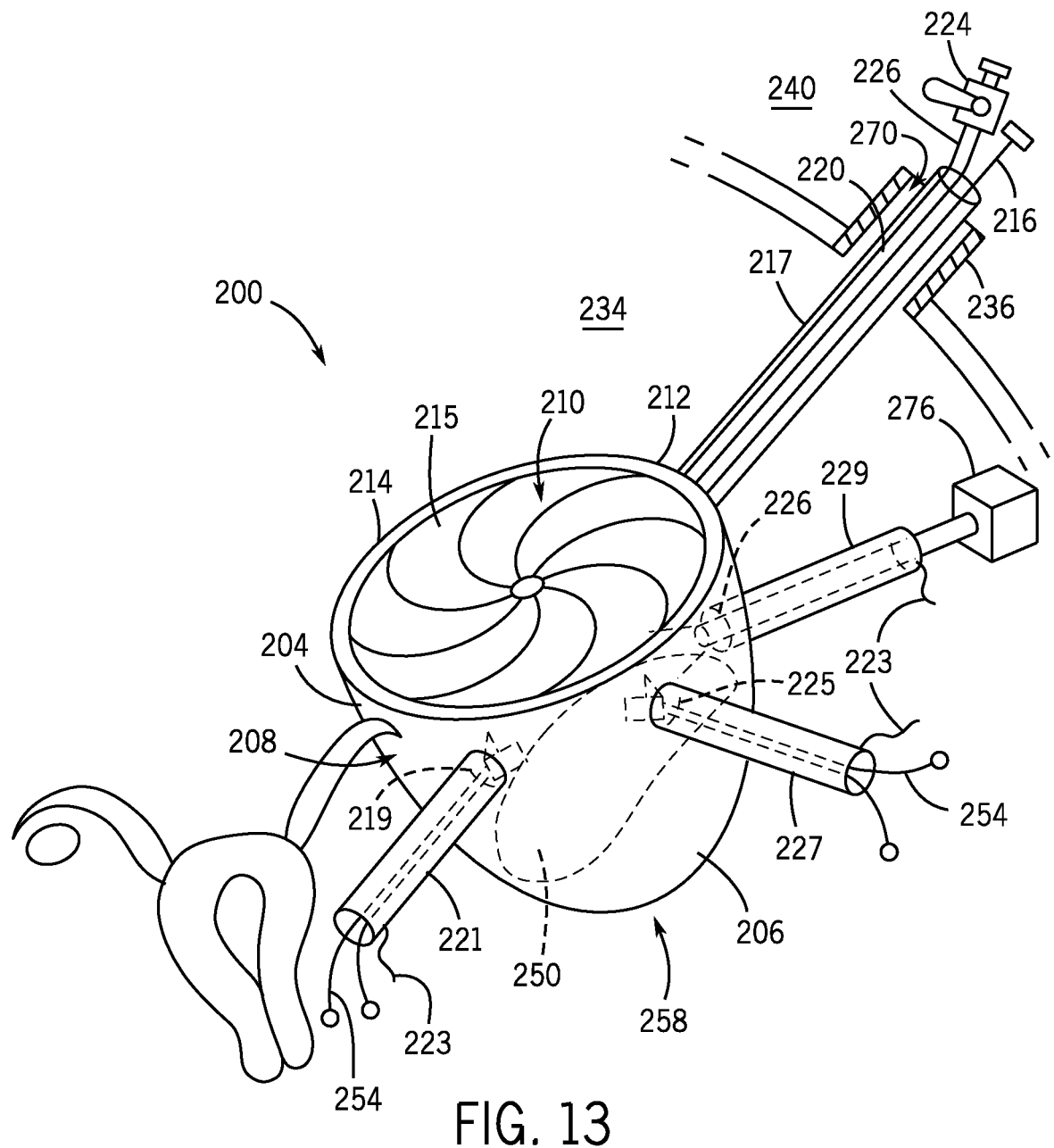
FIG. 13 is a side perspective view of the tissue retrieval device of FIG. 12 including a circular valve in a closed position.

Turning now to FIGS. 11-13, an alternative example retrieval device 200 for laparoscopic specimen retrieval is shown. The example retrieval device 200 is similar to the retrieval device 100 described above, and thus similar reference numerals will be used to describe the various components of the retrieval device 200. The retrieval device 200 is formed by a pouch 202 having a neck portion 204 and a pouch wall 206 downwardly extending therefrom. As shown in FIG. 12, an interior space 208 is defined by the pouch wall 206 for receiving a tissue mass 250, such as an adnexal mass and ovary, as shown in FIGS. 12-13. The pouch 202 includes an aperture 210 that circumscribes a perimeter 212 of the neck portion 204 and creates an opening for the retrieval device 200 to be placed around the tissue mass 250 within the interior space 208 of the pouch 202. A ring 214 constructed from a pliable material, for example, is coupled to the perimeter 212 of the neck portion 204 adjacent the pouch aperture 210 to provide rigidity to the rim and facilitates retrieval of the tissue mass 250 into the pouch 202, as will be described in further detail below.

A circular valve 215, as shown in FIG. 13, may be deployed from the ring 214 that helps keep the aperture 210 of the pouch 202 open. The circular valve 215 may be constructed from a pliable material, such as rubber or plastic, for example. A handle 217 may be coupled to the neck portion 204 of the pouch 202 to allow a user to manipulate the retrieval device 200 within the abdominal cavity 234 of the patient. Once the tissue mass 250 is retrieved into the retrieval device 200, a deployment mechanism 216 coupled to the handle 217 is activated to enclose the tissue mass 250 within the interior space 208 of the pouch 202 to prevent seeding, which may occur when tissue spills into the body of the patient, as shown in FIG. 13.

The pouch 202 is substantially spherical in shape and can be constructed from a nylon (e.g., ripstop nylon or a woven nylon) or polyvinyl chloride (PVC) material to help prevent any tearing that might occur during surgery, however any suitable material (e.g., a polypropylene material, a polyethylene material, a polyester material, an ethylene vinyl acetate (EVA) material, thermoplastic elastomers (TPEs), a Kevlar material, or an ultra-high molecular weight polyethylene (UHMWPE) material) can be used as an alternative. In some embodiments, the pouch 202 may be constructed from a transparent material, such that when a laparoscope is introduced into the abdominal cavity of the patient outside of the pouch 202, the surgery can be visualized through the transparent material. In other embodiments, the pouch 202 may be constructed from an opaque material.

In one example, the pouch 202 may include one or more access ports disposed on the pouch wall 206 to provide laparoscope visualization into the pouch 202. As shown in FIG. 12, a first access port 219 is provided on the pouch wall 206. An operating sleeve or access port sleeve 221 may be coupled to the first access port 219 and extend outwardly from the pouch wall 206. In addition, a tether 223 may be coupled to the access port sleeve 221 to allow an instrument, such as a grasper, to pull the access port sleeve 221 through an abdominal wall incision. Once the access port sleeve 221 is pulled through the incision, the access port sleeve 221 may be configured to receive an instrument, such as a laparoscope or tissue manipulation instrument, for visualization and manipulation of the specimen within the interior space 208 of the pouch 202. The access port 219 may have a self-sealing characteristic that enables the pouch wall 206 to be pierced by an instrument, such as a camera or laparoscope, and resealed after withdrawal of the instrument from the access port 219.

Similar to the first access port 219 and access port sleeve 221, the pouch 202 may include additional access port 225, 226 disposed on the pouch wall 206 and additional access port sleeves 227, 229 that extend outwardly from the pouch wall 206. In addition, tethers 223 may be coupled to the access port sleeves 227, 229 to allow an instrument, such as a grasper, to pull the access port sleeves 227, 229 through an abdominal wall incision. Once the access port sleeves 227, 229 is pulled through the incision, the access port sleeves 227, 229 may be configured to receive an instrument, such as a laparoscope or tissue manipulation instrument, for visualization and manipulation of the specimen within the interior space 208 of the pouch 202. The access ports 225, 226 may also have a self-sealing characteristic that enables the pouch wall 206 to be pierced by an instrument, such as a laparoscope, and resealed after withdrawal of the instrument from the access ports 225, 226.

The retrieval device 200 can further include an insufflation port 220 that is connected to an insufflator (not shown) and extends through the handle 217 to the aperture 210 and into the interior space 208 of the pouch. The insufflation port 220 may provide a non-flammable gas, such as carbon dioxide ($CO_2$), into the interior space 208 to insufflate the pouch 202 for visualization during the surgery. In some embodiments, a control valve 224 may be coupled to an end portion 226 of the insufflation port 220, such that when the pouch 202 is insufflated to a desired pressure, the control valve 224.

Still referring to FIGS. 11-13, the retrieval device 200 is intended to be used during an ovarian cystectomy, for example, that may be performed within the interior space 208 of the pouch 202 in order to avoid spillage of the tissue mass 250. This is of particular concern, for example, if the tissue mass 250 is malignant or includes one or more a dermoid cysts where spillage would cause chemical peritonitis, for example. The retrieval device 200 is introduced into the abdomen prior to the start of the procedure. The abdomen may be insufflated, or essentially blown up like a balloon, with carbon dioxide gas.

Prior to beginning the cystectomy, the retrieval device 200 may be provided in a retracted position for insertion into the abdominal cavity 234 of a patient using an insertion device, similar to that of the retrieval device 100 previously described. The retrieval device 200 is introduced into the abdominal cavity 234 via a trocar cannula 236 port, and once inserted into the abdominal cavity 234, the pliable ring 214 helps to keep the pouch 202 open. As best shown in FIG. 11, the pouch 202 remains in a retracted position 248, thus, the pouch 202 of the retrieval device 200 can be a pleated or rolled material as necessary to make an expandable configuration. The handle 217 of the retrieval device 200 may then be manipulated and placed around the tissue mass 250, as shown in FIG. 12. Upon capturing the tissue mass 250, the pouch 202 may expand from the retracted position 248, as shown in FIG. 11, to an extended position 258 caused by forces generated on the pouch 202 by the tissue mass 250.

Turning now to FIG. 13, once the tissue mass 250 is captured in the pouch 202, the deployment mechanism 216, coupled to the handle 217, may be activated to close the circular valve 215. The circular valve 215, when closed, allows the interior space 208 of the pouch 202 to be sealed from the abdominal cavity 234 to inhibit portions of the tissue mass 250 from entering the abdominal cavity 234 during the procedure. The pouch 202 is then insufflated to the fully extended position 258 via the insufflation port 220.

As previously described, the pouch 202 may have access ports 219, 225, and 226 incorporated into it that allow for punctures from various surgical instruments (e.g., camera, laparoscope, grasping instruments) into the pouch 202. Thus, the ovarian surgery can be performed inside the pouch 202 which avoids spillage from an ovarian cyst into the peritoneal cavity. As shown in FIG. 13, a camera 276 may be inserted through the access port sleeve 229 to visualize manipulation of the tissue mass 250 within the pouch 202. Alternatively, the camera 276 could be inserted through the other access port sleeves 221 or 227 to provide visualization into the pouch 202. Similarly, a grasping instrument 254 may be inserted through one or more of the access port sleeves 221, 227, 229 to manipulate the tissue mass 250 and perform the ovarian cystectomy, for example. Once the cystectomy has been completed, the trocars (not shown) are removed from the abdominal cavity 234, the access port sleeves 221, 227, 229 are sealed, and the pouch 202 and tissue mass 250 can be removed from the abdominal cavity 234 through an abdominal wall entry port 270.

Figure 14:
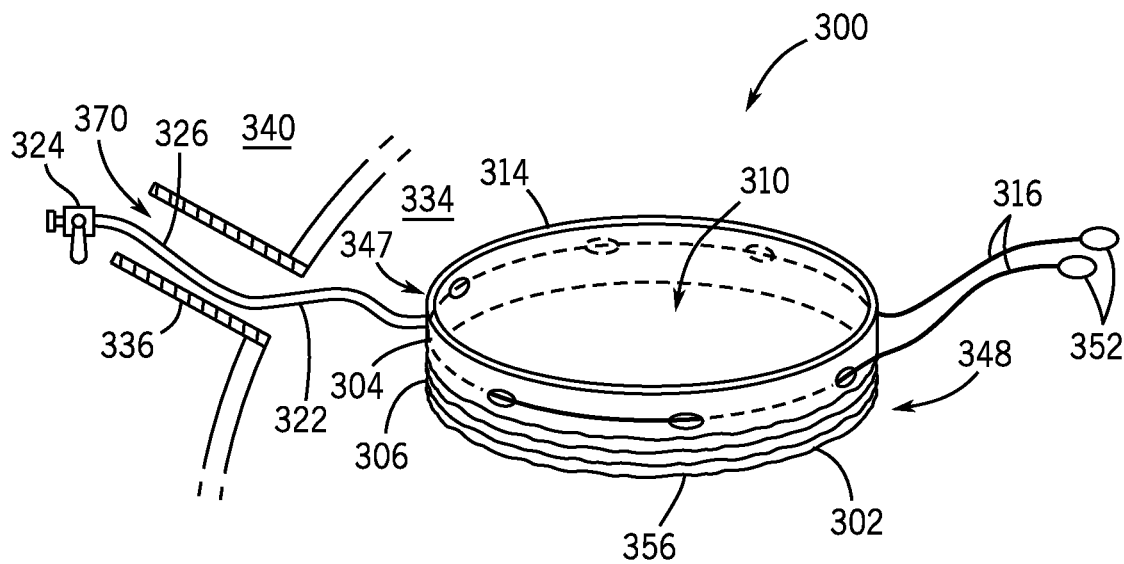
FIG. 14 is a side perspective view of a tissue retrieval device with a pouch and an inflatable rim in a retracted position.
Figure 15:
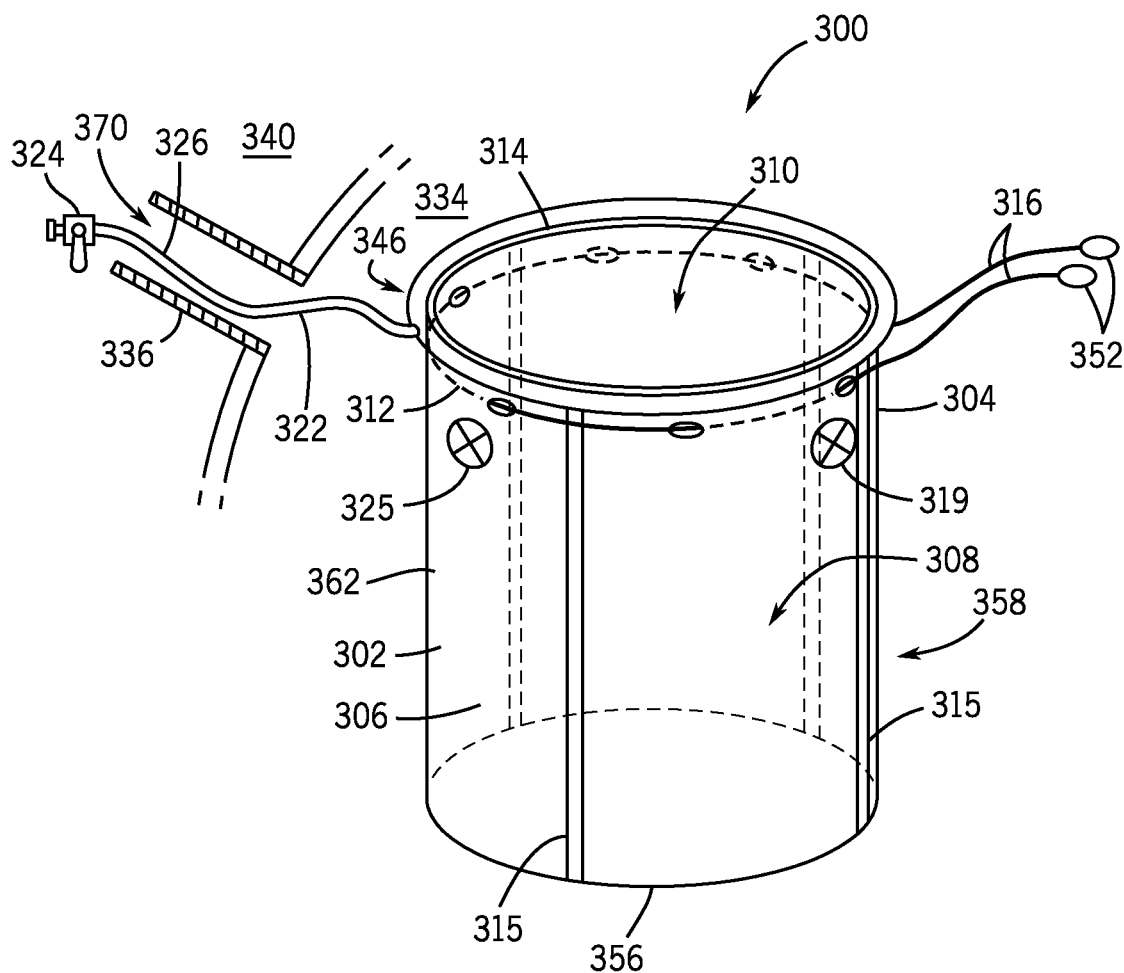
FIG. 15 is a side perspective view of the tissue retrieval device of FIG. 14 with the pouch and the inflatable rim in an expanded position.

Turning now to FIGS. 14-15, an alternative example retrieval device 300 for laparoscopic specimen retrieval is shown. The example retrieval device 300 is similar to the retrieval device 100, 200 described above, and thus similar reference numerals will be used to describe the various components of the retrieval device 300. The retrieval device 300 is formed by a pouch 302 having a neck portion 304 and a pouch wall 306 downwardly extending therefrom. As shown in FIG. 15, an interior space 308 is defined by the pouch wall 306 for receiving tissue masses (not shown). The pouch 302 includes an aperture 310 that circumscribes a perimeter 312 of the neck portion 304 and creates an opening for placement of the tissue masses within the interior space 308 of the pouch 302. An inflatable rim 314 is coupled to the perimeter 312 of the neck portion 304 adjacent the pouch aperture 310. A plurality of inflatable, longitudinal ribs 315 may be linked to the inflatable rim 314 and extend along the pouch wall 306. Thus, when insufflated, the inflatable rim 314 and the plurality of longitudinal ribs 315 provide rigidity to the pouch 302 and facilitate retrieval of the tissue specimens into the pouch 302. Once the tissue specimens are retrieved into the retrieval device 300, a drawstring-like closure device 316 coupled to the neck portion 304 of the pouch wall 306 is activated to enclose the tissue specimens within the interior space 308 of the pouch 302 to prevent seeding, which may occur when tissue spills into the body of the patient.

Figure 16A:
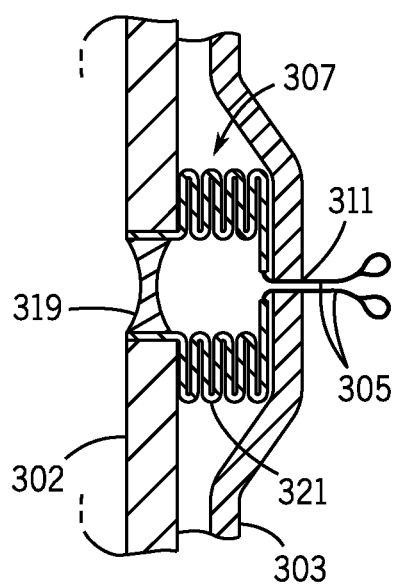
FIG. 16A is a partial side cross-sectional view of an access port sleeve of the tissue retrieval device of FIG. 14 in a collapsed position.
Figure 16B:
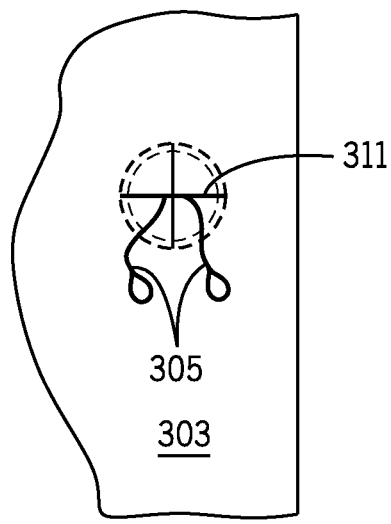
FIG. 16B is a partial top plan view of the access port sleeve of FIG. 16A.

Additionally, the pouch 302 may include one or more access ports disposed on the pouch wall 306 to provide laparoscope visualization and/or instrument introduction into the pouch 302. As shown in FIG. 16, a first access port 319 and a second access port 325 are provided in a collapsed state on the pouch wall 306. An access port sleeve 321, as shown in FIGS. 16A-16B, may be coupled to the first access port 319 in a collapsed state 307. An access port sleeve (not shown) may also be coupled to the second access port 325. In some embodiments, the pouch 302 may be formed from a single thickness of material. However, as shown in FIG. 16A, an outer bag 303 may surround the pouch 302. Thus, a double lining may be provided where the inner bag 302 provides a material with properties different than the pouch 302 such as tear strength, porosity, manufacturability and ductility. The first access port 319 may also provide a seal, as shown in FIG. 16A, between the access port sleeve 321 and the pouch 302.

Figure 17:
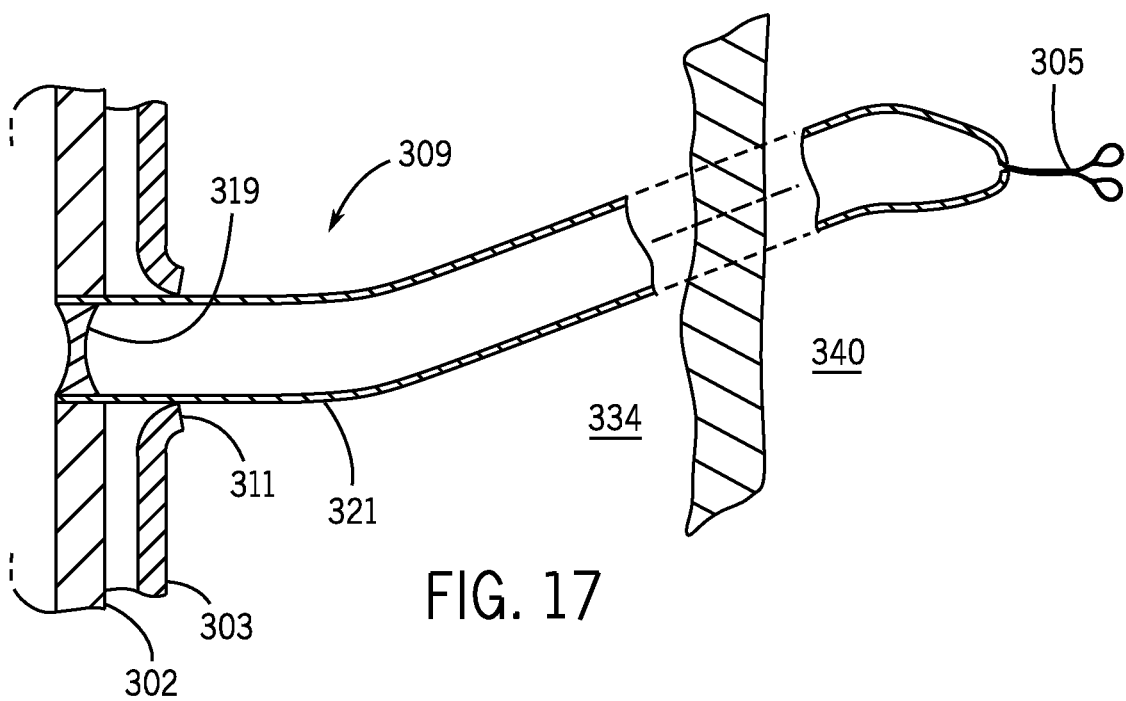
FIG. 17 is a partial side cross-sectional view of the access port sleeve of FIG. 16A in an expanded position.

Still referring to FIGS. 16A-16B, the access port sleeve 321 may include drawstrings 305, for example, for unfolding the access port sleeve 321 from the collapsed state 307 to an expanded state 309, as shown in FIG. 17. The drawstrings 305 may be grasped by a grasping instrument 154 (see FIG. 6), for example to grasp and unfurl the access port sleeve 321 through an abdominal incision from the abdominal cavity 334 to the external environment 340. The drawstrings 305 may also provide the ability to seal the access port sleeve 321 once it has been contaminated with cellular materials (i.e., tissue masses). In some embodiments, a cross-slit port 311 may be provided on the outer bag 303 to enable the removal of the collapsed access port sleeve 321. Once the access port sleeve 321 is in the expanded state 309, a trocar cannula (not shown) may be placed into the expanded access port sleeve 321. An instrument, such as a laparoscope or endoscope, may then be introduced into the sealed passageway created by the trocar cannula and expanded access port sleeve 321. The instrument may be pushed past the first access port 319, which may be provided in the form of a flap or cross-cut valve, and into the pouch 302 to provide direct visualization. Thus, since the instrument is introduced and removed within a contiguous sleeve, any contamination of the instrument may be constrained to remain with the access port sleeve 321.

Figure 18A:
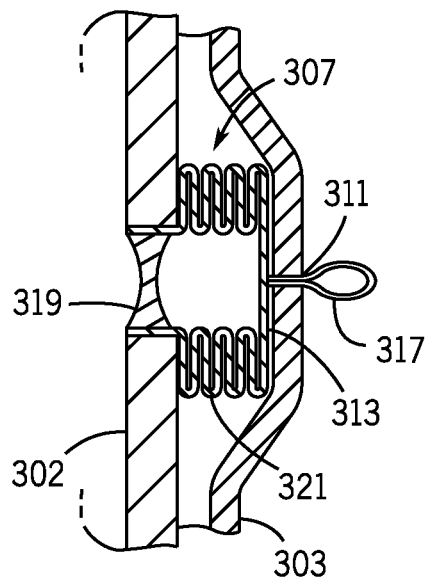
FIG. 18A is a partial side cross-sectional view of another access port sleeve of the tissue retrieval device of FIG. 14 in a collapsed position.
Figure 18B:
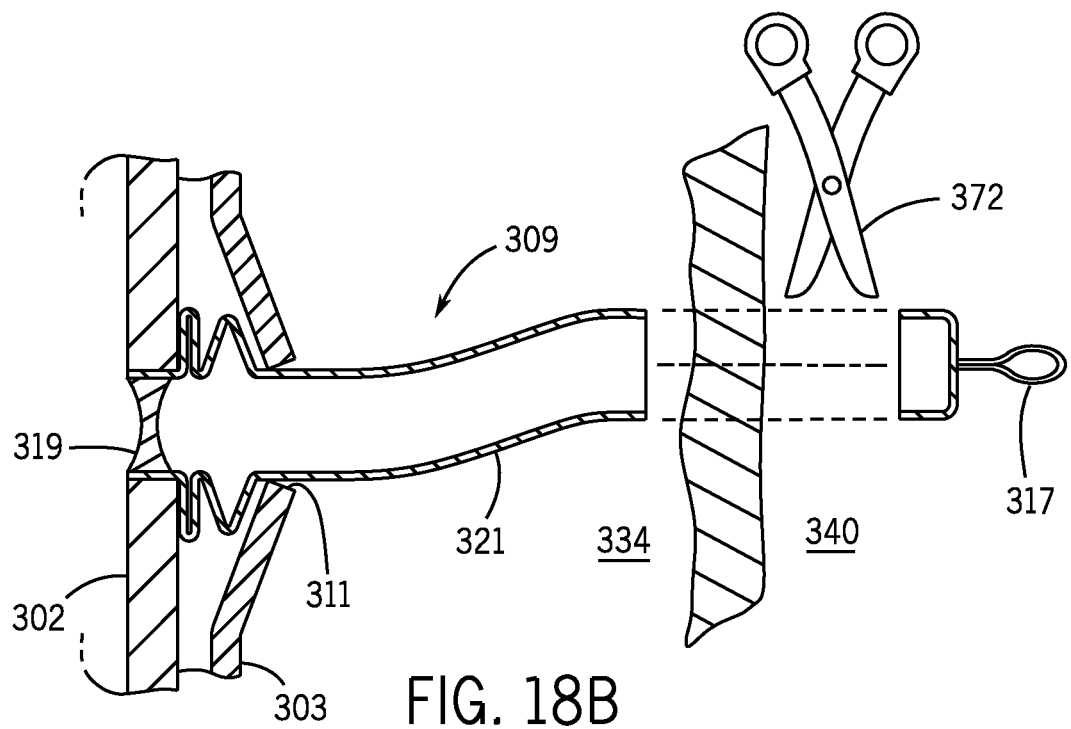
FIG. 18B is a partial side cross-sectional view of the access port sleeve of FIG. 19A in an expanded position.

In an alternative embodiment, as shown in FIGS. 18A-18B, the drawstrings 305 described with respect to FIGS. 16A, 16B and 17 may be replaced with a loop or tag 317 coupled to the access port sleeve 321 in the form of a sealed cap, for example. The tag 317 may be grasped by a grasping instrument 154 (see FIG. 6), to grasp and unfurl the access port sleeve 321 through an abdominal port from the abdominal cavity 334 to the external environment 340. Once the access port sleeve 321 is in the expanded position 309, as shown in FIG. 18B, the tag 317 may be cut using a cutting instrument 372, to open the sealed passage created by the access port sleeve 321. As previously described, a trocar cannula (not shown) may then be placed into the expanded access port sleeve 321. An instrument, such as a laparoscope or endoscope, may then be introduced into the sealed passageway created by the trocar cannula and expanded access port sleeve 321. The instrument may be pushed past the first access port 319 and into the pouch 302 to provide direct visualization.

Returning to FIGS. 14 and 15, the retrieval device 300 can further include an inflation port 322 connected to the inflatable rim 314 and the plurality of longitudinal ribs 315 for inflation purposes. In some embodiments, the inflation port 322 may be releasably coupled to the inflatable rim 314. A control valve 324 may be coupled to an end portion 326 of the inflation port 322, such that when the inflatable rim 314 and the plurality of longitudinal ribs 315 are inflated to a desired pressure, the control valve 324 may be closed to prevent the rim 314 and the plurality of longitudinal ribs 315 from deflating. In some embodiments, the control valve 324 may be provided in the form of a flap, a duck-billed valve, or the like.

Similar to the previously described retrieval device 100, the retrieval device 300 is also intended to be used during surgery after tissue has been resected in order to remove specimens from the abdomen. The retrieval device 300 is introduced into the abdomen prior to the start of the procedure. The abdomen may be insufflated, or essentially blown up like a balloon, with carbon dioxide gas. Once the retrieval device 300 is introduced into the abdominal cavity 334 via the trocar cannula 336 port, the inflatable rim 314 and the plurality of longitudinal ribs 315 are inflated using the inflation port 322 connected to a laparoscopic insufflator (not shown). As the inflatable rim 314 and the plurality of longitudinal ribs 315 are inflated, the rim 314 expands from the retracted position 347 to an inflated, extended position 346, and the pouch 302 expands from the retracted position 348 to the expanded position 358.

Once the inflatable rim 314 and the plurality of longitudinal ribs 315 are inflated to the desired pressure, the control valve 324 can be closed and pushed into the abdominal cavity 134. Tissue specimens (not shown) may then be placed into the retrieval device 300 using a grasping instrument (not shown) inserted through the trocar cannula 336. When the procedure is completed (i.e., the tissue specimens have been retrieved), end portions 352 of the drawstring-like closure device 316 can be grasped and pulled upward using one or more grasping instruments to exteriorize the end portions 352 of the drawstring-like closure device 316 and the neck portion 304 of the pouch 302 from the abdominal cavity 334.

As previously described, because the tissue may be too large to fit through the abdominal wall entry port 370, a morcellator and grasping instrument may be introduced into the pouch 302 to reduce the tissue volume. After the tissue is morcellated using the morcellator, the pouch 302 and morcellated tissue (not shown) can be removed from the abdominal cavity 334 through the abdominal wall entry port 270.

Figure 19:
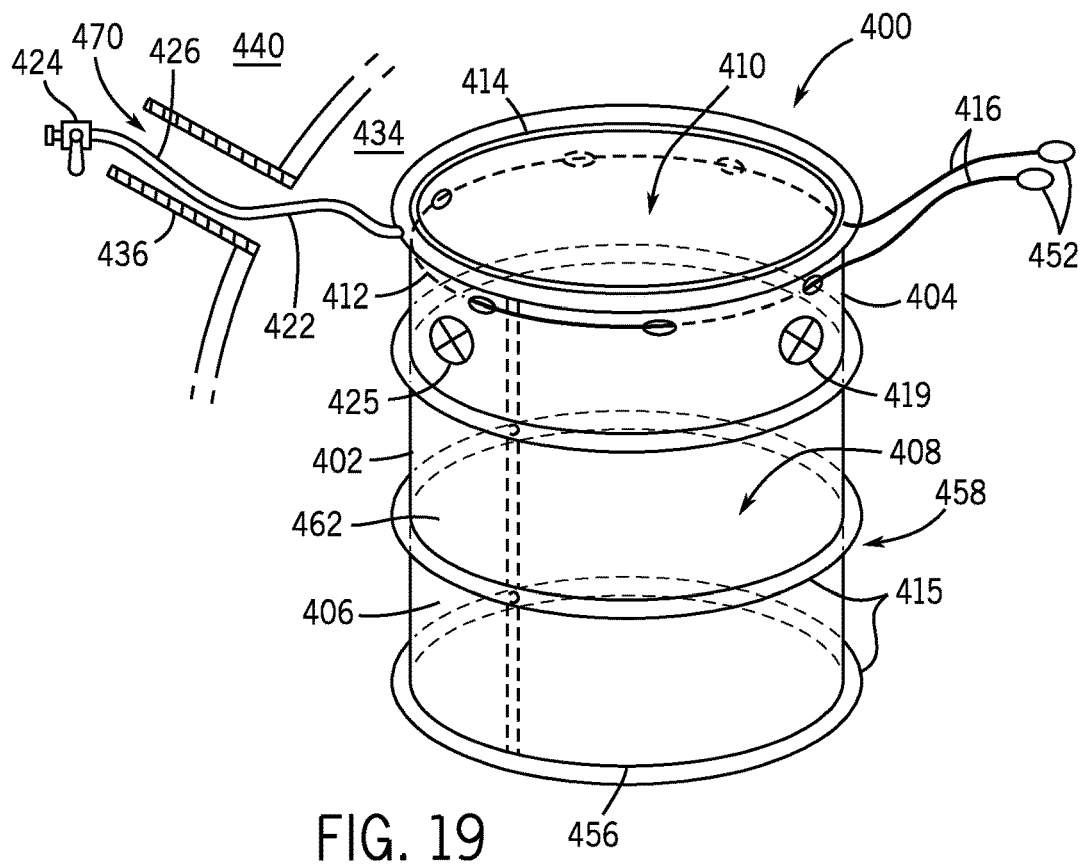
FIG. 19 is a side perspective view of another tissue retrieval device with a pouch and an inflatable rim in an expanded position.

Turning now to FIG. 19, an alternative example retrieval device 400 for laparoscopic specimen retrieval is shown. The example retrieval device 400 is similar to retrieval devices 100, 200, and 300 described above, and thus similar reference numerals will be used to describe the various components of the retrieval device 400. The retrieval device 400 is formed by a pouch 402 having a neck portion 404 and a pouch wall 406 downwardly extending therefrom. An interior space 408 is defined by the pouch wall 406 for receiving tissue masses (not shown). The pouch 402 includes an aperture 410 that circumscribes a perimeter 412 of the neck portion 404 and creates an opening for placement of the tissue masses within the interior space 408 of the pouch 402. An inflatable rim 414 is coupled to the perimeter 412 of the neck portion 404 adjacent the pouch aperture 410. A plurality of inflatable, radial ribs 415 may be linked to the inflatable rim 414 and extend along the circumference of the pouch wall 406. Thus, when insufflated, the inflatable rim 414 and the plurality of radial ribs 415 provide rigidity to the pouch 402 and facilitates retrieval of the tissue specimens into the pouch 402. Once the tissue specimens are retrieved into the retrieval device 400, a drawstring-like closure device 416 coupled to the neck portion 404 of the pouch wall 406 is activated to enclose the tissue specimens within the interior space 408 of the pouch 402.

Figure 20:
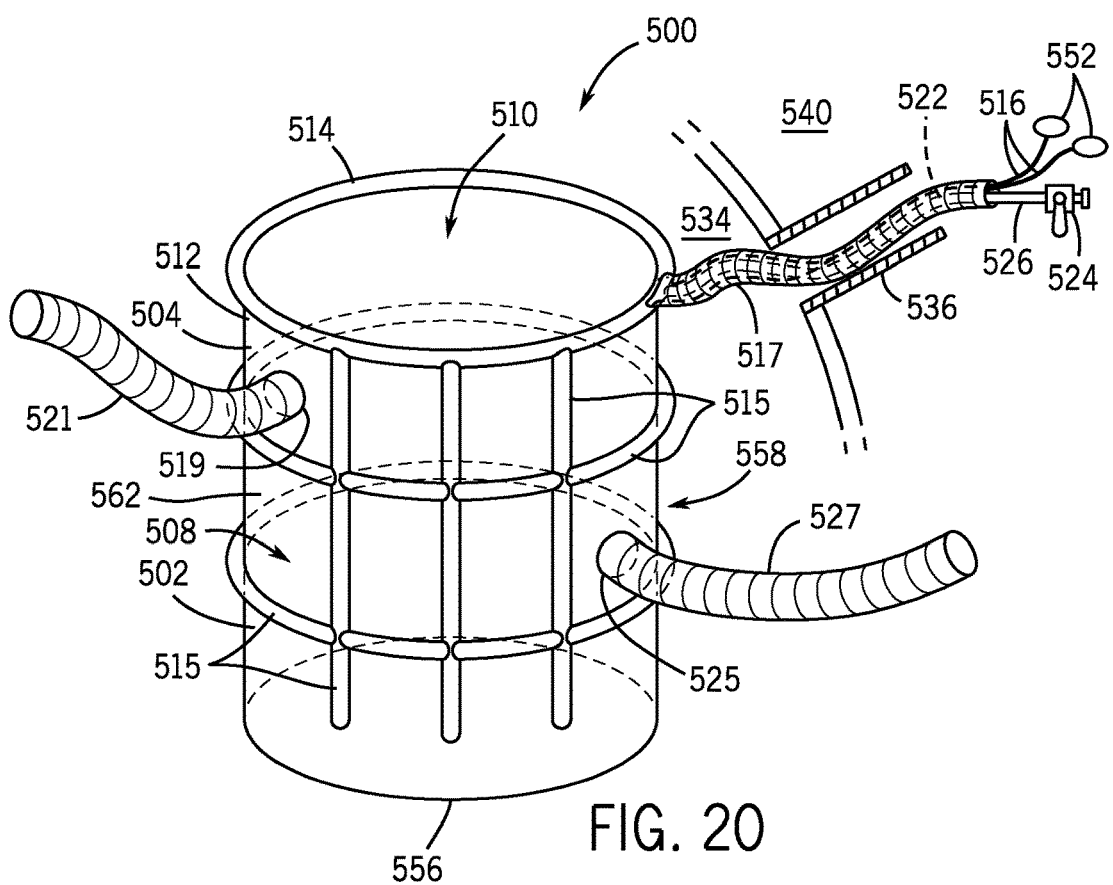
FIG. 20 is a side perspective view of another tissue retrieval device with a pouch and an inflatable rim in an expanded position.

In yet another embodiment, as shown in FIG. 20, an example retrieval device 500 includes both longitudinal and radial inflatable ribs 515 coupled to the inflatable rim 514. The retrieval device 500 may include similar components and features as described with respect to retrieval devices 300, 400, therefore similar reference numerals are provided in FIG. 20.

Figure 21:
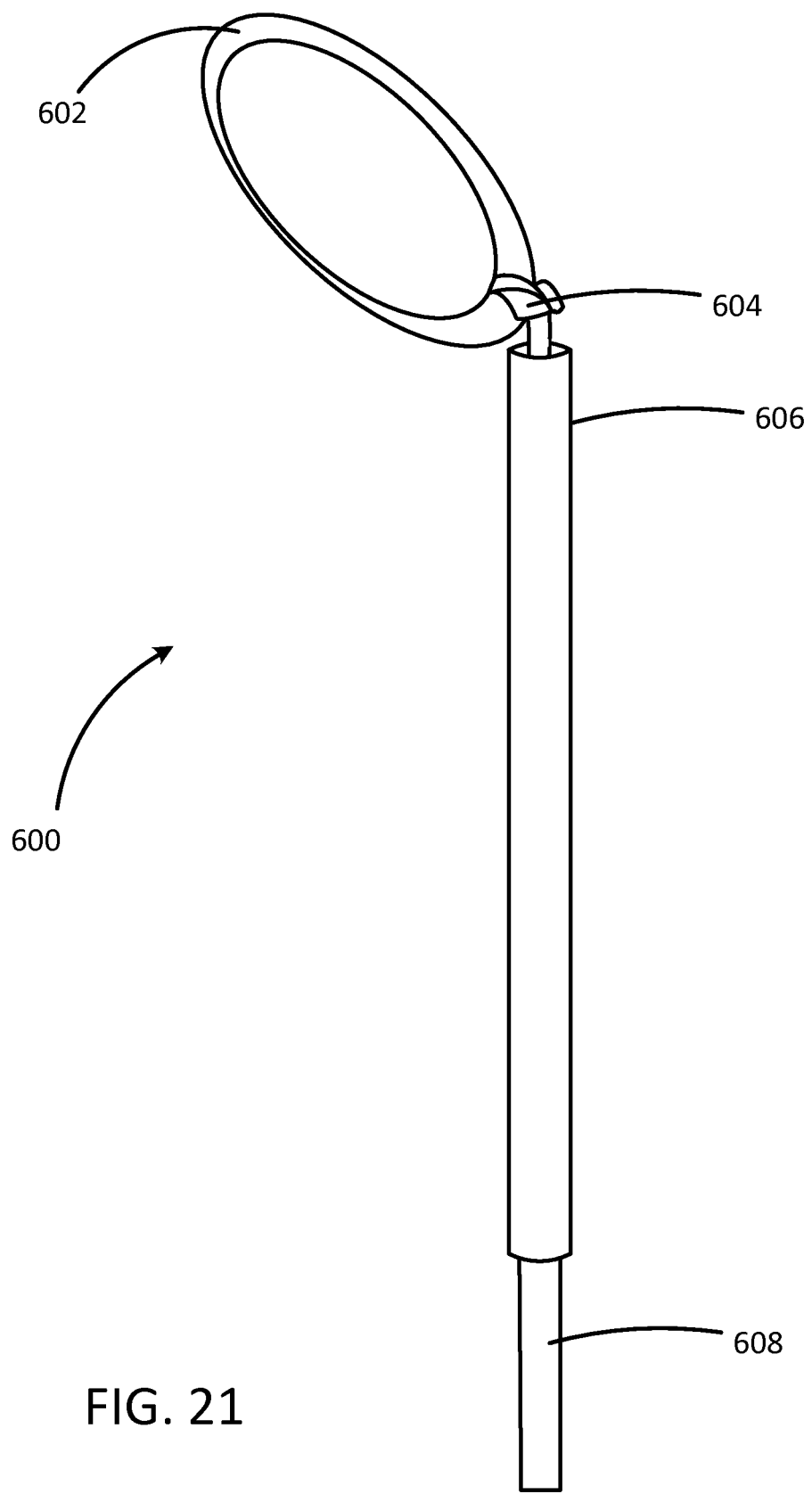
FIG. 21 is a side view of closure device suitable for closing an aperture or access sleeve of a tissue retrieval device.

Turning now to FIG. 21, an example of a closure device 600 that may be used with any embodiment of the retrieval devices 100, 200, 300, 400, and 500 is shown. The illustrated closure device 600 can include a loop 602 coupled to a knot 604, a stopping element 606, and an elongated element 608.

The knot 604 may be configured to slide on the elongated element 608. The stopping element 606 may define a substantially hollow cylinder configured so the knot 604 cannot pass through the stopping element 606. The loop 602, the knot 604, and the elongated element 608 may be fabricated from a fibrous strand, string, or band, in one embodiment. In other embodiments, the loop 602, the knot 604, and the elongated element 608 may be fabricated from a metal strand, string, or band.

In operation, the elongated element 608 can be pulled until the knot 604 engages the stopping element 606. The elongated element 608 can then continue to be pulled so the elongated element 608 slides along the knot 604 collapsing the loop 602.

Figure 22:
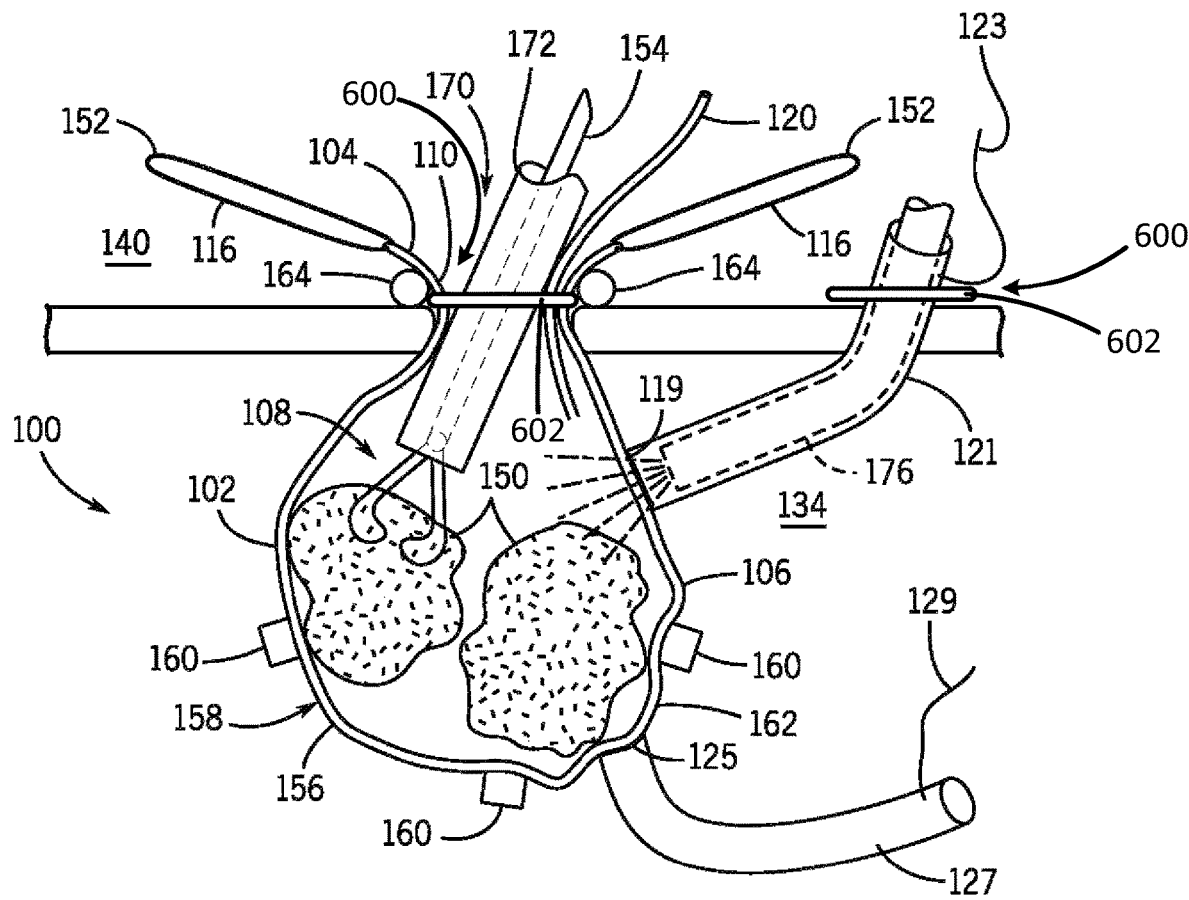
FIG. 22 is a side view of the closure device of FIG. 21 closing an aperture and an access sleeve of a tissue retrieval device.

Turning now to FIG. 22, an example of the closure device 600 in use with the example retrieval device 100 for laparoscopic specimen retrieval is shown. The closure device 600 can be coupled to the pouch wall 106 by placing the loop 602 around the pouch wall 106 adjacent to the neck portion 104. Once the tissue specimens are retrieved into the retrieval device 100 and the morcellator 172 is removed, the loop 602 can be collapsed enclosing the tissue 150 within the interior space 108 of the pouch 102 preventing leakage of the tissue specimen or other residual cells or bacteria from the pouch 102. The closure device 600 can also be coupled to an open end of the upper access port sleeve 121 by surrounding the open end of the upper access port sleeve 121 with the loop 602. Once the tissue specimens are retrieved into the retrieval device 100 and the laparoscope 176 is removed, the loop 602 can be collapsed enclosing the open end of the upper access port sleeve 121 preventing leakage of the tissue specimen or other residual cells or bacteria from the upper access port sleeve 121. Although not shown in FIG. 22, the closure device 600 may also be coupled to an open end of the lower access port sleeve 127, as desired.

Figure 23:
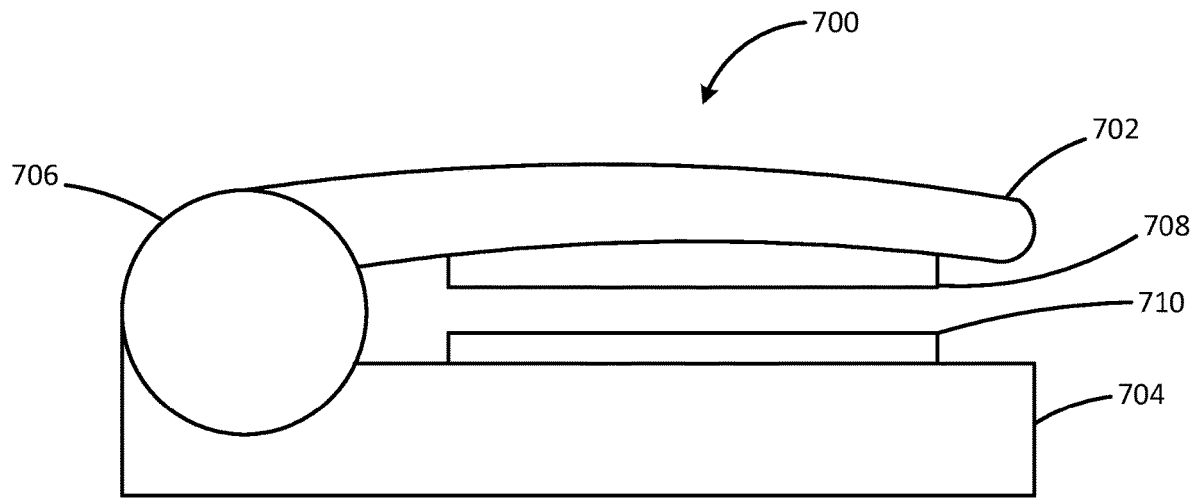
FIG. 23 is a side view of another closure device suitable for closing an aperture or access sleeve of a tissue retrieval device.

Turning now to FIG. 23, an alternative example of a closure device 700 that may be used with any embodiment of the retrieval devices 100, 200, 300, 400, and 500 is shown. The illustrated closure device 700 includes a first body member 702 and a second body member 704. The first body member 702 is coupled to a rotatable joint 706 allowing the first body member 702 to be moveable with respect to the second body member 704. The first body member 702 includes a first resistive heating element 708 and the second resistive body member 704 includes a second heating element 710.

In operation, a sealable member (not shown) defining an open end that may include a first side and a second side can be placed between the first heating element 708 and the second heating element 710. A force can be applied to the first body member 702 and/or the second body member 704 causing the first body member 702 to displace rotatively using the rotatable joint 706. The first body member 702 will continue to displace rotatively the first heating element 708 contacts the second heating element 710 compressing the open end of the sealable member therebetween. The first heating element 708 and/or the second heating element 710 can be turned on by means of a switch (not shown) or a plug (not shown) heating the open end of the sealable member. The open end is heated until the first side and the second side of the open end are fused together forming a pressure tight seal. The illustrated closure device 700 may be portable, wireless, and/or handheld for ease of use during laparoscopic tissue retrieval.

Figure 24:
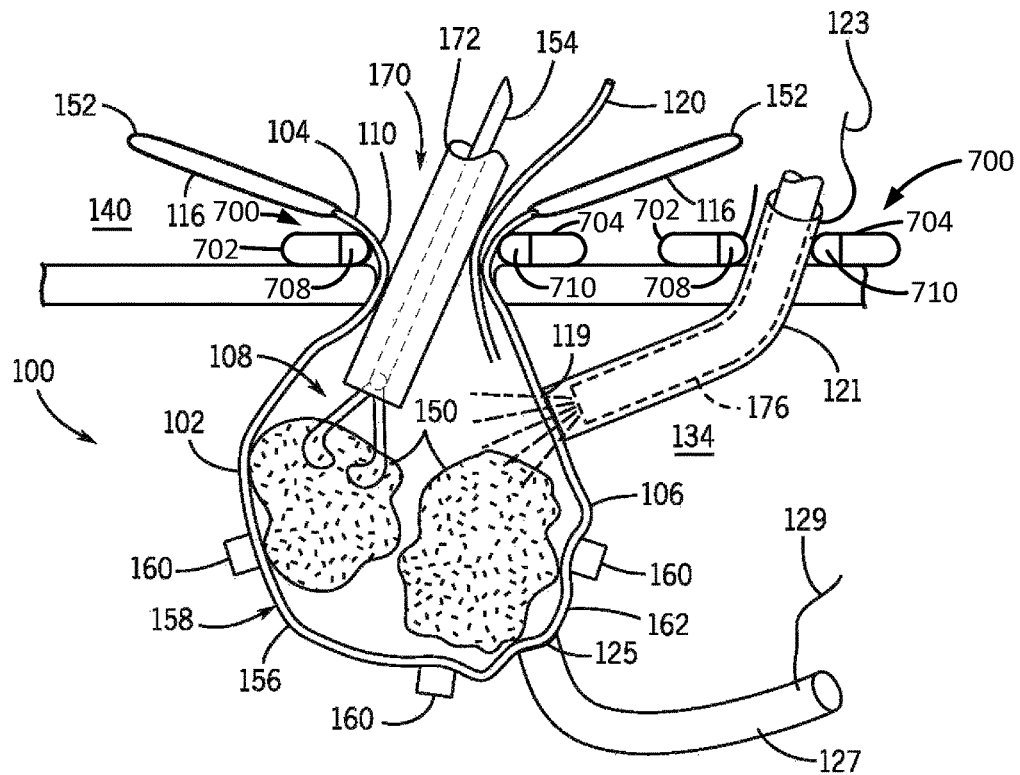
FIG. 24 is a side view of the closure device of FIG. 23 closing an aperture and an access sleeve of a tissue retrieval device.

Turning now to FIG. 24, an example of the closure device 700 in use with the example retrieval device 100 for laparoscopic specimen retrieval. The closure device 700 can be used to seal the pouch wall 106 by placing the aperture 110 between the first heating element 708 and the second heating element 710. Once the tissue specimens are retrieved into the retrieval device 100 and the morcellator 172 is removed, two sides of the pouch wall 106 can be compressed together between the first heating element 708 and the second heating element 710. Then the first heating element 708 and/or the second heating element 710 can be turned heating the pouch wall 106 until the two sides of the pouch wall 106 are fused together sealing the pouch 102. This would provide a pressure tight seal preventing leakage of the tissue specimen or other residual cells or bacteria from the pouch 102. The closure device 700 can be used to seal an open end of the upper access port sleeve 121 by placing the open end of the upper access port sleeve 121 between the first heating element 708 and the second heating element 710. Once the tissue specimens are retrieved into the retrieval device 100 and the laparoscope 176 is removed, two sides of the open end of the upper access port sleeve 121 can be compressed together between the first heating element 708 and the second heating element 710. Then the first heating element 708 and/or the second heating element 710 can be turned on thereby heating the open end of the upper access port sleeve 121 until the two sides of the open end of the upper access port sleeve 121 are fused together. This would provide a pressure tight seal preventing leakage of the tissue specimen or other residual cells or bacteria from the upper access port sleeve 121. Although not shown in FIG. 22, the closure device 700 may also be used to seal an open end of the lower access port sleeve 127, as desired.

The present retrieval devices 100, 200, 300, 400, and 500 described above have advantages over conventional tissue retrieval devices. First, the present retrieval devices facilitate tissue morcellation while minimizing residual debris in the abdominal cavity. Second, the present retrieval devices provide a completely enclosed laparoscopic specimen removal. In addition, there are no available enclosed systems for ovarian surgery. Currently, patients either have laparoscopic surgery with an enclosed morcellator for tissue mass reduction and risk contamination of malignant cells or they have a laparotomy that also carries a risk of contamination and also is associated with more morbidity and longer recovery time. The present retrieval device could also be expanded to include other surgical procedures in other cavities and for other indications including, but not limited to, total laparoscopic hysterectomy (TLH), laparoscopic supracervical hysterectomy (LSH), laparoscopic myomectomy (LM), laparoscopic bowel resections and other internal viscera where the risk of losing cells during tissue capture and removal poses a risk to the patient.

What is claimed is:

1. A retrieval device for removing tissue, the retrieval device comprising:
   a pouch including an aperture and a pouch wall extending therefrom, the pouch having an interior space defined by the pouch wall;
   an access port sleeve having a first end and an opposite open second end, the first end of the access port sleeve being connected to the pouch wall, the access port sleeve extending outwardly from the pouch wall and dimensioned and configured to receive a laparoscope for manipulation or visualization of the tissue, the open second end of the access port sleeve being configured and dimensioned to receive the laparoscope;
   a first closure device for enclosing the tissue within the interior space of the pouch;

a second closure device for closing the open second end of the access port sleeve, the second closure device comprising a loop at an end of an elongated element in which a knot slides on the elongated element to make the loop collapsible; and an access port disposed on the pouch wall, wherein the access port sleeve surrounds the access port, and wherein the access port has a self-sealing characteristic so that upon removal of the laparoscope back through the access port, the access port reseals" after "to make the loop collapsible.

2. The retrieval device of claim 1, wherein the pouch is configured to be at least one of folded, rolled and pleated for placement within an insertion device prior to deployment into a patient.

3. The retrieval device of claim 1, further comprising at least one tab coupled to an exterior portion of the pouch wall, the at least one tab configured to be engaged by an instrument to expand the pouch wall from a retracted position to an expanded position.

4. The retrieval device of claim 1, wherein the first closure device is provided by drawstrings encompassing at least a portion of the pouch wall, the drawstrings, upon activation, generate a force between the tissue and the pouch wall, thereby causing the pouch wall to expand from a retracted position to an expanded position.

5. The retrieval device of claim 1, further comprising:
an inflatable rim coupled to the aperture of the pouch to facilitate retrieval of the tissue into the interior space of the pouch; and
an insufflation connector coupled to the inflatable rim, and wherein the insufflation connector is configured to insufflate the inflatable rim, thereby providing a rigid rim surrounding the aperture of the pouch.

6. The retrieval device of claim 1, wherein the laparoscope is configured to pierce the self-sealing characteristic of the access port for visualization of the tissue within the interior space of the pouch.

7. The retrieval device of claim 1, wherein the pouch is constructed of at least one of a transparent material, an opaque material, a ripstop nylon material, a woven nylon material, a polypropylene material, a polyethylene material, a polyester material, a polyvinyl chloride (PVC) material, an ethylene vinyl acetate (EVA) material, thermoplastic elastomers (TPEs), a Kevlar material, and an ultra high molecular weight polyethylene (UHMWPE) material.

8. The retrieval device of claim 1, wherein the retrieval device is devoid of additional pouches.

9. The retrieval device of claim 1, further comprising a sealing cap dimensioned to seal the aperture of the pouch, the sealing cap including an insufflation connector configured to insufflate the interior space of the pouch.

10. The retrieval device of claim 1, wherein the access port sleeve is a first access port sleeve, and further comprising a second access port sleeve connected to the pouch wall at one end and configured to receive a laparoscope at an opposing end of the second access port sleeve, and
wherein the laparoscope is configured to be received through the entirety of the second access port.

11. The retrieval device of claim 1, further comprising a tether connected to a surface of the access port sleeve.

12. The retrieval device of claim 1, further comprising:
an inflatable rim coupled to the aperture of the pouch;
an inflation port in fluid communication with the inflatable rim, the inflation port being configured to receive a fluid to inflate the inflatable rim;
a control valve in fluid communication with the inflatable rim, the control valve being configured to prevent deflation of the inflatable rim; and
an insufflation port in fluid communication with the interior space of the pouch, the insufflation port configured to receive and provide a fluid to the interior space, and wherein the control valve is disposed in a patient after the inflatable rim is inflated.

13. The retrieval device of claim 1, further comprising:
an outer bag encapsulating the access port sleeve, the access port sleeve being in a collapsed configuration; and
at least one of a drawstring, a loop, or a tag, coupled to a surface of the access port sleeve, and
wherein a grasping instrument is configured to grasp the at least one of the drawstring, the loop, or the tag to expand the access port sleeve from the collapsed configuration to an expanded configuration.

14. The retrieval device of claim 13, further comprising:
another port disposed on the outer bag,
wherein the another port retains the access port sleeve in the collapsed configuration, and
wherein the access port sleeve is received through the another port in the expanded configuration.

15. A retrieval device for removing tissue, the retrieval device comprising:
a pouch including an aperture and a pouch wall extending therefrom, the pouch having an interior space defined by the pouch wall;
an inflatable rim coupled to the aperture of the pouch to facilitate retrieval of the tissue into the interior space of the pouch;
a control valve in fluid communication with the inflatable rim, the control valve being configured to prevent deflation of the inflatable rim, the control valve is configured to be disposed in a patient after the inflatable rim is inflated;
a closure device coupled to the pouch wall for enclosing the tissue within the interior space of the pouch, the closure device being disposed below the inflatable rim and below the aperture of the pouch; and
an access port sleeve having a first end and an opposite second end, the first end of the access port sleeve being connected to the pouch wall, the access port sleeve extending outwardly from the pouch wall and dimensioned and configured to receive a laparoscope for manipulation or visualization of the tissue, the second end of the access port sleeve being configured and dimensioned to receive the laparoscope, a portion of the access port sleeve is configured to be disposed within the patient when the pouch is disposed within the patient,
wherein the pouch is configured to move from a retracted position to an expanded position upon inflation of the inflatable rim, and
wherein the closure device is configured to be activated to enclose the tissue within the interior space of the pouch, when the inflatable rim has been inflated.

16. A retrieval device for removing tissue, the retrieval device comprising:
a pouch including an aperture and a pouch wall extending therefrom, the pouch having an interior space defined by the pouch wall;
an inflatable rim coupled to the aperture of the pouch to facilitate retrieval of the tissue into the interior space of the pouch;

a control valve in fluid communication with the inflatable rim, the control valve being configured to prevent deflation of the inflatable rim, the control valve being disposed in a patient after the inflatable rim is inflated;

a closure device coupled to the pouch wall for enclosing the tissue within the interior space of the pouch; and an access port sleeve having a first end and an opposite second end, the first end of the access port sleeve being connected to the pouch wall, the access port sleeve extending outwardly from the pouch wall and dimensioned and configured to receive a laparoscope for manipulation or visualization of the tissue, the second end of the access port sleeve being configured and dimensioned to receive the laparoscope, and wherein the entirety of the access port sleeve is configured to be disposed within the patient when the pouch is disposed within the patient.

17. A retrieval device for removing tissue, the retrieval device comprising:

a pouch including an aperture and a pouch wall extending therefrom, the pouch having an interior space defined by the pouch wall, the aperture of the pouch being at a first location of the pouch;

an access port sleeve having a first end and an opposite open second end, the first end of the access port sleeve being connected to the pouch wall at a second location of the pouch that is different than the first location of the pouch, the access port sleeve extending outwardly from the pouch wall and dimensioned and configured to receive a laparoscope for manipulation or visualization of the tissue, the open second end of the access port sleeve being configured and dimensioned to receive the laparoscope;

an access port disposed on the pouch wall, the access port sleeve surrounding the access port, and the access port having a self-sealing characteristic so that upon removal of the laparoscope back through the access port, the access port reseals; and a closure device for closing the open second end of the access port sleeve, the closure device comprising a loop at an end of an elongated element in which a knot slides on the elongated element to make the loop collapsible.

18. The retrieval device of claim 17, further comprising a second access port sleeve coupled to the pouch wall and configured to receive an instrument for manipulation or visualization of the tissue.

19. The retrieval device of claim 17, further comprising:

an inflatable rim coupled to the aperture of the pouch to facilitate retrieval of the tissue into the interior space of the pouch; and a control valve in fluid communication with the inflatable rim, the control valve being configured to prevent deflation of the inflatable rim, the control valve being disposed in a patient after the inflatable rim is inflated.

20. A retrieval device comprising:

a pouch including a neck portion defining an aperture, and a pouch wall extending therefrom, the pouch wall having an exterior portion and defining an interior space, the pouch being configured to receive tissue specimens within the interior space;

a tab disposed on the exterior portion of the pouch wall, and wherein grasping of the tab with a grasper expands the pouch wall;

an access port sleeve having a first end and an opposite open second end, the first end of the access port sleeve being connected to the pouch wall, the access port sleeve extending outwardly from the pouch wall and dimensioned and configured to receive a laparoscope for manipulation or visualization of the tissue, the open second end of the access port sleeve being configured and dimensioned to receive the laparoscope; an access port disposed on the pouch wall, wherein the access port sleeve surrounds the access port, and wherein the access port has a self-sealing characteristic so that upon removal of the laparoscope back through the access port, the access port reseals" after "to receive the laparoscope; and a closure device for closing the open second end of the access port sleeve, the closure device comprising a loop at an end of an elongated element in which a knot slides on the elongated element to make the loop collapsible.

21. A retrieval device comprising:

a pouch including a neck portion defining an aperture, and a pouch wall extending therefrom, the pouch wall having an exterior portion and defining an interior space, the pouch being configured to receive tissue specimens within the interior space;

an access port sleeve having a first end and an opposite second end, the first end of the access port sleeve being connected to the pouch wall, the access port sleeve extending outwardly from the pouch wall and dimensioned and configured to receive a laparoscope for manipulation or visualization of the tissue, the second end of the access port sleeve being configured and dimensioned to receive the laparoscope; an access port disposed on the pouch wall, wherein the access port sleeve surrounds the access port, and wherein the access port has a self-sealing characteristic so that upon removal of the laparoscope back through the access port, the access port reseals" after "to receive the laparoscope; and a tether connected to a surface of the access port sleeve.

22. The retrieval device of claim 21, further comprising:

an inflatable rim coupled to the aperture of the pouch to facilitate retrieval of the tissue into the interior space of the pouch; and a control valve in fluid communication with the inflatable rim, the control valve being configured to prevent deflation of the inflatable rim, the control valve being disposed in a patient after the inflatable rim is inflated.

* * * * *

UNITED STATES PATENT AND TRADEMARK OFFICE
CERTIFICATE OF CORRECTION

PATENT NO. : 11,172,913 B2
APPLICATION NO. : 15/101162
DATED : November 16, 2021
INVENTOR(S) : James Greenberg et al.

It is certified that error appears in the above-identified patent and that said Letters Patent is hereby corrected as shown below:

In the Claims

Column 19, Claim 1, Line 10, "reseals" after "to receive the laparoscope;" should be --reseals;--.

Column 22, Claim 20, Line 8, "and wherein grasping" should be --and grasping--.

Column 22, Claim 20, Lines 21-22, "reseals" after "to receive the laparoscope;" should be --reseals;--.

Column 22, Claim 21, Lines 44-45, "reseals" after "to receive the laparoscope;" should be --reseals;--.

Signed and Sealed this
Thirty-first Day of May, 2022

Katherine Kelly Vidal
*Director of the United States Patent and Trademark Office*